US012694661B2

(12) United States Patent
Agrawal et al.

(10) Patent No.: US 12,694,661 B2
(45) Date of Patent: Jul. 28, 2026

(54) EXPLAINABLE VISUAL ATTENTION FOR DEEP LEARNING

(71) Applicant: GE Precision Healthcare LLC, Waukesha, WI (US)

(72) Inventors: Utkarsh Agrawal, Bengaluru (IN); Bipul Das, Chennai (IN); Prasad Sudhakara Murthy, Bengaluru (IN)

(73) Assignee: GE PRECISION HEALTHCARE LLC, Waukesha, WI (US)

( * ) Notice: Subject to any disclaimer, the term of this patent is extended or adjusted under 35 U.S.C. 154(b) by 351 days.

(21) Appl. No.: 18/482,085

(22) Filed: Oct. 6, 2023

(65) Prior Publication Data

US 2025/0118062 A1     Apr. 10, 2025

(51) Int. Cl.
| | |
|---|---|
| *G06V 10/82* | (2022.01) |
| *G06V 10/77* | (2022.01) |
| *G16H 30/20* | (2018.01) |

(52) U.S. Cl.
CPC .......... *G06V 10/82* (2022.01); *G06V 10/7715* (2022.01); *G16H 30/20* (2018.01)

(58) Field of Classification Search
None
See application file for complete search history.

(56) References Cited

U.S. PATENT DOCUMENTS

| | | | | |
|---|---|---|---|---|
| 10,997,433 | B2 * | 5/2021 | Xu ......................... | G06V 20/41 |
| 2017/0236057 | A1 * | 8/2017 | Lane ................... | G06V 10/764 |
| | | | | 706/25 |

| | | | | |
|---|---|---|---|---|
| 2017/0270664 | A1 * | 9/2017 | Hoogi ................. | A61B 6/5217 |
| 2019/0332932 | A1 * | 10/2019 | Sivaraman .............. | G06N 3/08 |
| 2019/0365341 | A1 * | 12/2019 | Chan ..................... | G06T 7/0012 |
| 2022/0058803 | A1 * | 2/2022 | Bhattacharya ........... | G06T 7/37 |
| 2022/0101635 | A1 * | 3/2022 | Koivisto ............. | G05D 1/0246 |
| 2022/0284570 | A1 * | 9/2022 | Tan ......................... | G06N 3/09 |
| 2022/0327810 | A1 * | 10/2022 | Nagori ................ | G06N 3/0464 |

(Continued)

FOREIGN PATENT DOCUMENTS

| | | |
|---|---|---|
| CN | 115393246 A | 11/2022 |
| JP | 2021022368 A | 2/2021 |

OTHER PUBLICATIONS

Watanabe et al., "Improving Disease Classification Performance and Explainability of Deep Learning Models in Radiology with Heatmap Generators," Jun. 2022, https://arxiv.org/pdf/2207.00157 (Year: 2022).*

(Continued)

*Primary Examiner* — Soo Shin

(74) *Attorney, Agent, or Firm* — Amin, Turocy & Watson, LLP

(57) ABSTRACT

Systems or techniques that facilitate explainable visual attention for deep learning are provided. In various embodiments, a system can access a medical image generated by a medical imaging scanner. In various aspects, the system can perform, via execution of a deep learning neural network, an inferencing task on the medical image. In various instances, the deep learning neural network can receive as input the medical image and can produce as output both an inferencing task result and an attention map indicating on which pixels or voxels of the medical image the deep learning neural network focused in generating the inferencing task result.

14 Claims, 14 Drawing Sheets

(56)                    References Cited

U.S. PATENT DOCUMENTS

| | | | |
|---|---|---|---|
| 2022/0383489 A1* | 12/2022 | Shi | G06N 3/084 |
| 2023/0137369 A1* | 5/2023 | Balicki | A61B 8/5207 |
| | | | 600/437 |

OTHER PUBLICATIONS

Qurri et al., "Improved UNet with Attention for Medical Image Segmentation," Sensors 2023, 23, 8589. https://doi.org/10.3390/s23208589 (Year: 2023).*

Huang, Z. et al. l "A novel tongue segmentation method based on improved U-Net." Neurocomputing, vol. 500, Aug. 21, 2022, pp. 73-89, 17 pages.

Rengasamy, D. et al. l "Deep Learning with Dynamically Weighted Loss Function for Sensor-Based Prognostics and Health Management." Sensors (Basel). Jan. 28, 2020;20(3):723. doi: 10.3390/s20030723. PMID: 32012944; PMCID: PMC7038523, 21 pages.

Akino Watanabe et al: "Improving Disease Classification Performance and Explainability of Deep Learning Models in Radiology with Heatmap Generators", arxiv.org, Cornell University Library, 201OLIN Library Cornell University Ithaca, NY, XP091260531, * Sec. 221, 2.1.1 *.

CN 115393246 English Abstract; Espacenet.com; 1 page.

Cristiano Patr\'icio et al: "Explainable Deep Learning Methods in Medical Imaging Diagnosis: A Survey", arxiv.org, Cornell University Library, 201, Olin Library Cornell University Ithaca, NY, XP091245323, * the whole document *.

EP application 242007391 filed Sep. 17, 2024—extended Search Report issued Feb. 21, 2025; 25 pages.

Xiaozheng Xie et al: "A Survey on Domain Knowledge Powered Deep Learning for Medical Image Analysis", arxiv.org, Cornell University Library, Olin Library Cornell University Ithaca, NY, 14853, XP081652902 Sec. 2.3.3; * abstract; figure 5 *.

JP application 2024-161572 filed Sep. 19, 2024—Office Action issued on Dec. 3, 2025; Machine Translation; 4 pages.

JP2021-022368 English Abstract, Espacenet.com Feb. 26, 2026; 1 page.

* cited by examiner

FIG. 3

210
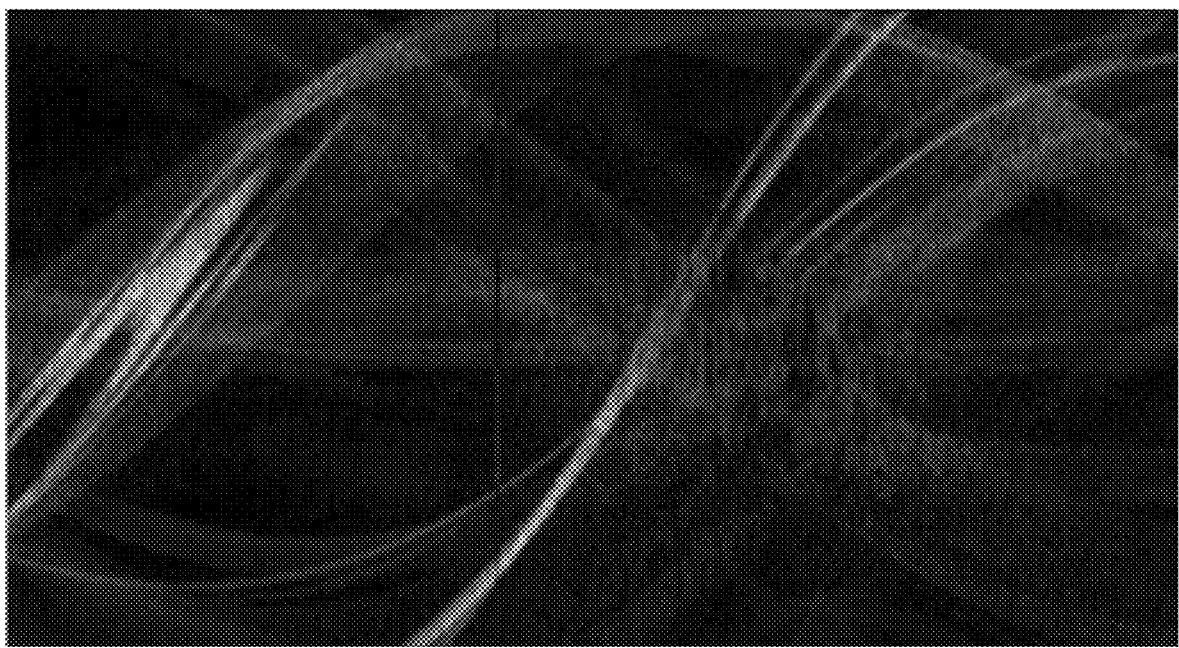
104
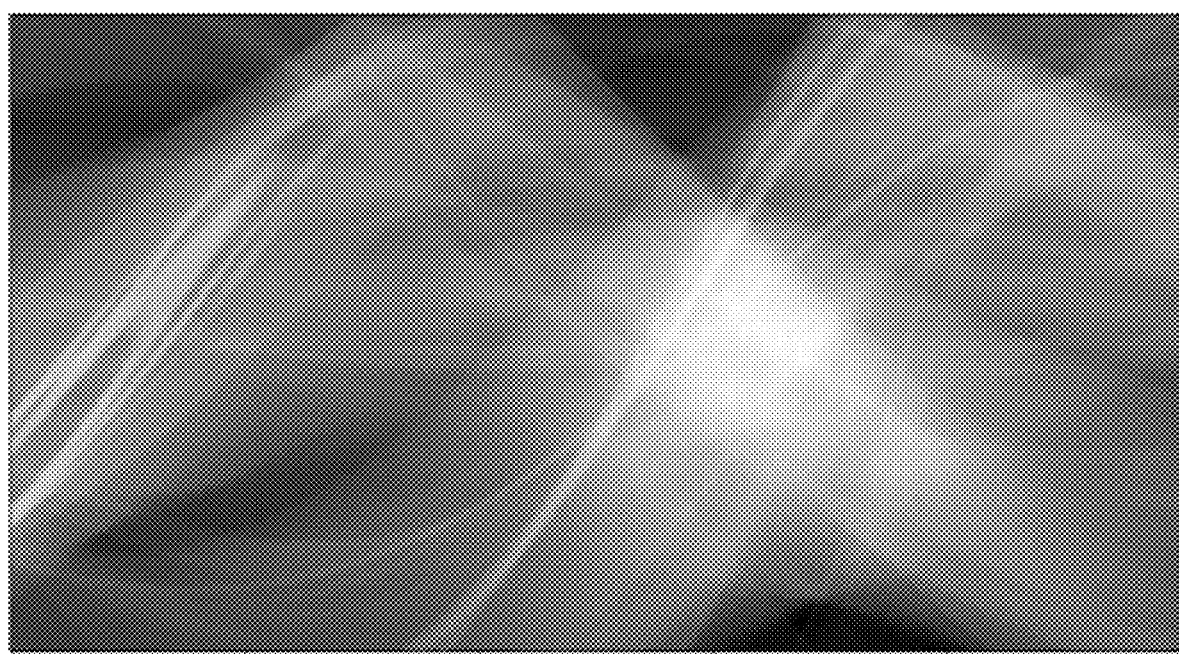
FIG. 4

210
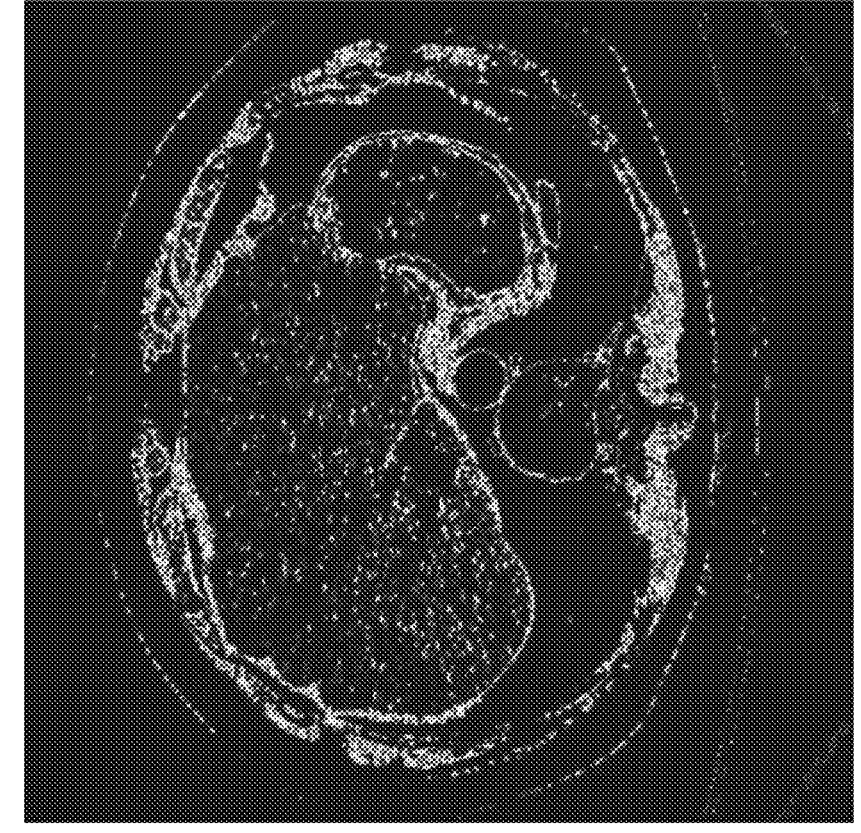
104
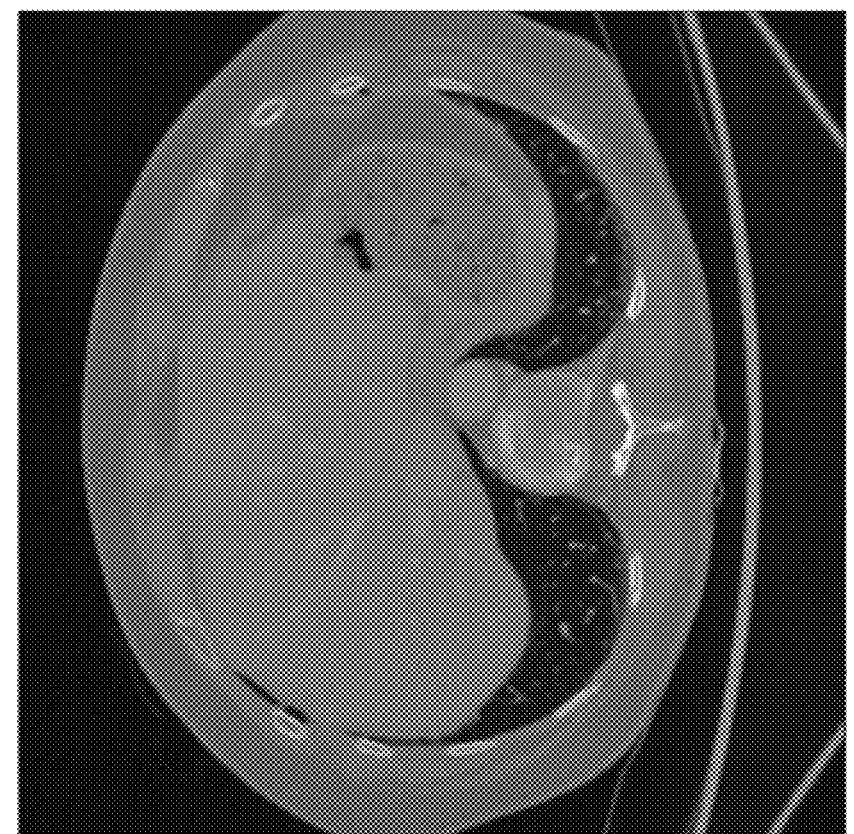
FIG. 5

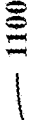
1100
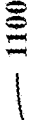
FIG. 11

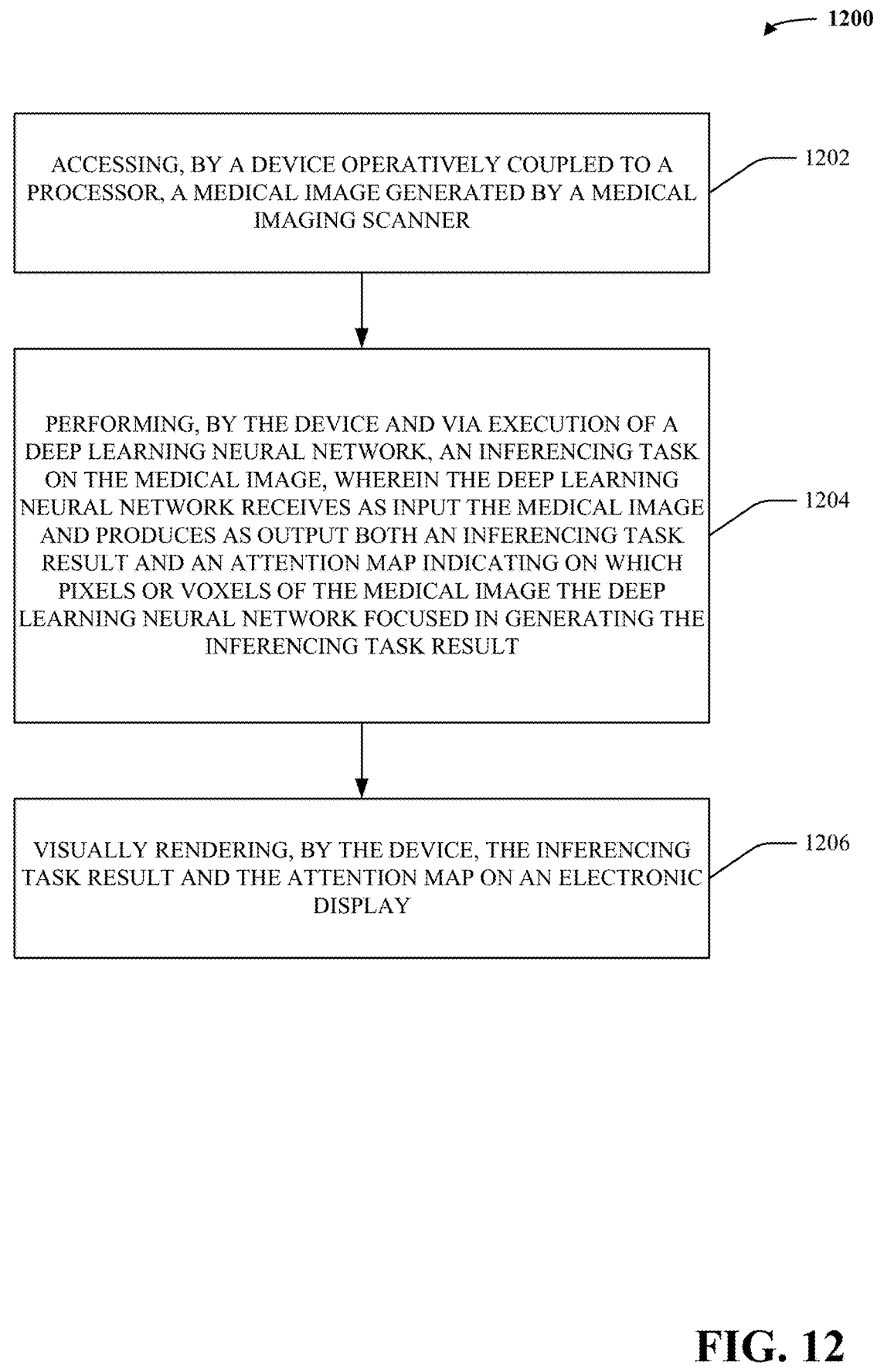

1200

ACCESSING, BY A DEVICE OPERATIVELY COUPLED TO A PROCESSOR, A MEDICAL IMAGE GENERATED BY A MEDICAL IMAGING SCANNER ⟵ 1202

PERFORMING, BY THE DEVICE AND VIA EXECUTION OF A DEEP LEARNING NEURAL NETWORK, AN INFERENCING TASK ON THE MEDICAL IMAGE, WHEREIN THE DEEP LEARNING NEURAL NETWORK RECEIVES AS INPUT THE MEDICAL IMAGE AND PRODUCES AS OUTPUT BOTH AN INFERENCING TASK RESULT AND AN ATTENTION MAP INDICATING ON WHICH PIXELS OR VOXELS OF THE MEDICAL IMAGE THE DEEP LEARNING NEURAL NETWORK FOCUSED IN GENERATING THE INFERENCING TASK RESULT ⟵ 1204

VISUALLY RENDERING, BY THE DEVICE, THE INFERENCING TASK RESULT AND THE ATTENTION MAP ON AN ELECTRONIC DISPLAY ⟵ 1206

FIG. 12

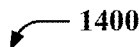
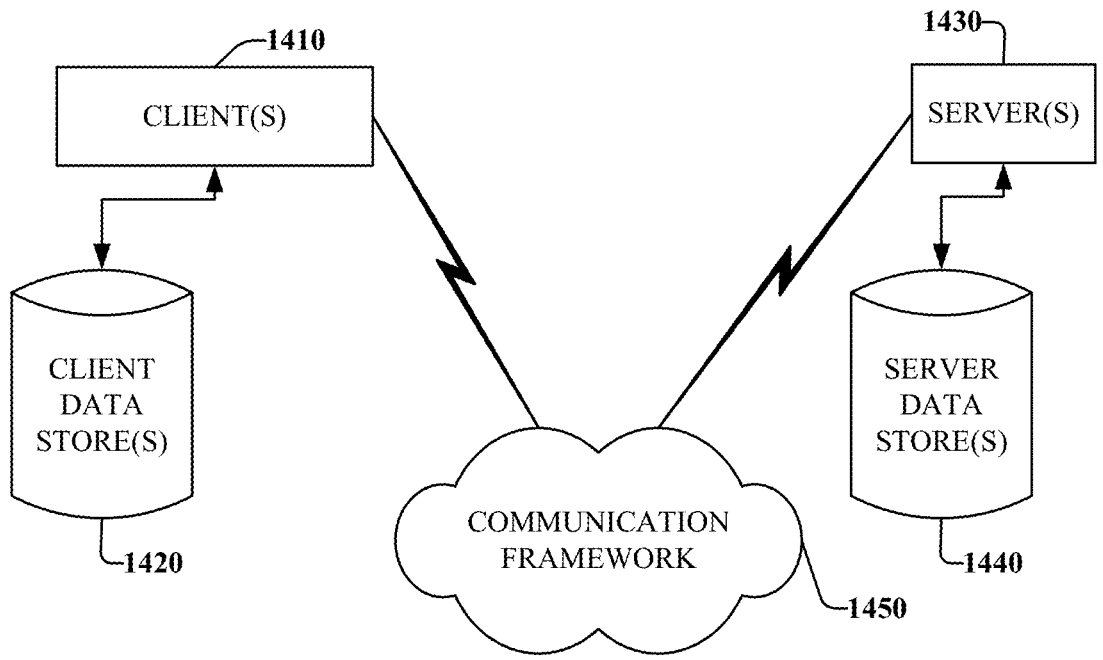
FIG. 14

EXPLAINABLE VISUAL ATTENTION FOR DEEP LEARNING

TECHNICAL FIELD

The subject disclosure relates generally to deep learning, and more specifically to explainable visual attention for deep learning.

BACKGROUND

A deep learning neural network can be trained to perform an inferencing task on a medical image. When performing the inferencing task, it can be desired for the deep learning neural network to pay closer attention to certain portions of the medical image than to other portions of the medical image. Unfortunately, existing techniques for facilitating such attention are insufficiently interpretable or explainable.

Accordingly, systems or techniques that can facilitate deep learning attention for medical images with heightened interpretability or explainability can be desirable.

SUMMARY

The following presents a summary to provide a basic understanding of one or more embodiments. This summary is not intended to identify key or critical elements, or delineate any scope of the particular embodiments or any scope of the claims. Its sole purpose is to present concepts in a simplified form as a prelude to the more detailed description that is presented later. In one or more embodiments described herein, devices, systems, computer-implemented methods, apparatus or computer program products that facilitate explainable visual attention for deep learning are described.

According to one or more embodiments, a system is provided. The system can comprise a non-transitory computer-readable memory that can store computer-executable components. The system can further comprise a processor that can be operably coupled to the non-transitory computer-readable memory and that can execute the computer-executable components stored in the non-transitory computer-readable memory. In various embodiments, the computer-executable components can comprise an access component that can access a medical image generated by a medical imaging scanner. In various aspects, the computer-executable components can comprise an execution component that can perform, via execution of a deep learning neural network, an inferencing task on the medical image. In various instances, the deep learning neural network can receive as input the medical image and can produce as output both an inferencing task result and an attention map indicating on which pixels or voxels of the medical image the deep learning neural network focused in generating the inferencing task result.

According to one or more embodiments, a computer-implemented method is provided. In various embodiments, the computer-implemented method can comprise accessing, by a device operatively coupled to a processor, a medical image generated by a medical imaging scanner. In various aspects, the computer-implemented method can comprise performing, by the device and via execution of a deep learning neural network, an inferencing task on the medical image. In various instances, the deep learning neural network can receive as input the medical image and can produce as output both an inferencing task result and an attention map indicating on which pixels or voxels of the medical image the deep learning neural network focused in generating the inferencing task result.

According to one or more embodiments, a computer program product for facilitating explainable visual attention for deep learning is provided. In various embodiments, the computer program product can comprise a non-transitory computer-readable memory having program instructions embodied therewith. In various aspects, the program instructions can be executable by a processor to cause the processor to access a deep learning neural network comprising a primary processing channel, wherein the primary processing channel can be trained, using a set of training images and a set of ground-truth inferencing task results respectively corresponding to the set of training images, to perform an inferencing task. In various instances, the program instructions can be further executable to cause the processor to insert an auxiliary processing channel into the deep learning neural network, such that the auxiliary processing channel branches off from, and is parallel to at least a portion of, the primary processing channel. In various cases, the program instructions can be further executable to cause the processor to train, using a set of ground-truth attention maps respectively corresponding to the set of training images, the auxiliary processing channel to produce pixel-wise or voxel-wise attention maps indicating where within inputted images the deep learning neural network focuses when performing the inferencing task.

DESCRIPTION OF THE DRAWINGS

FIG. 3 illustrates an example, non-limiting block diagram showing how a deep learning neural network can produce an inferencing task result and an attention map in accordance with one or more embodiments described herein.

FIGS. 4-5 illustrate example, non-limiting instances of medical images and corresponding attention maps in accordance with one or more embodiments described herein.

FIGS. 9-11 illustrate example, non-limiting experimental results regarding explainable visual attention for deep learning in accordance with one or more embodiments described herein.

FIG. 12 illustrates a flow diagram of an example, non-limiting computer-implemented method that facilitates explainable visual attention for deep learning in accordance with one or more embodiments described herein.

FIG. 14 illustrates an example networking environment operable to execute various implementations described herein.

DETAILED DESCRIPTION

Figure 1:
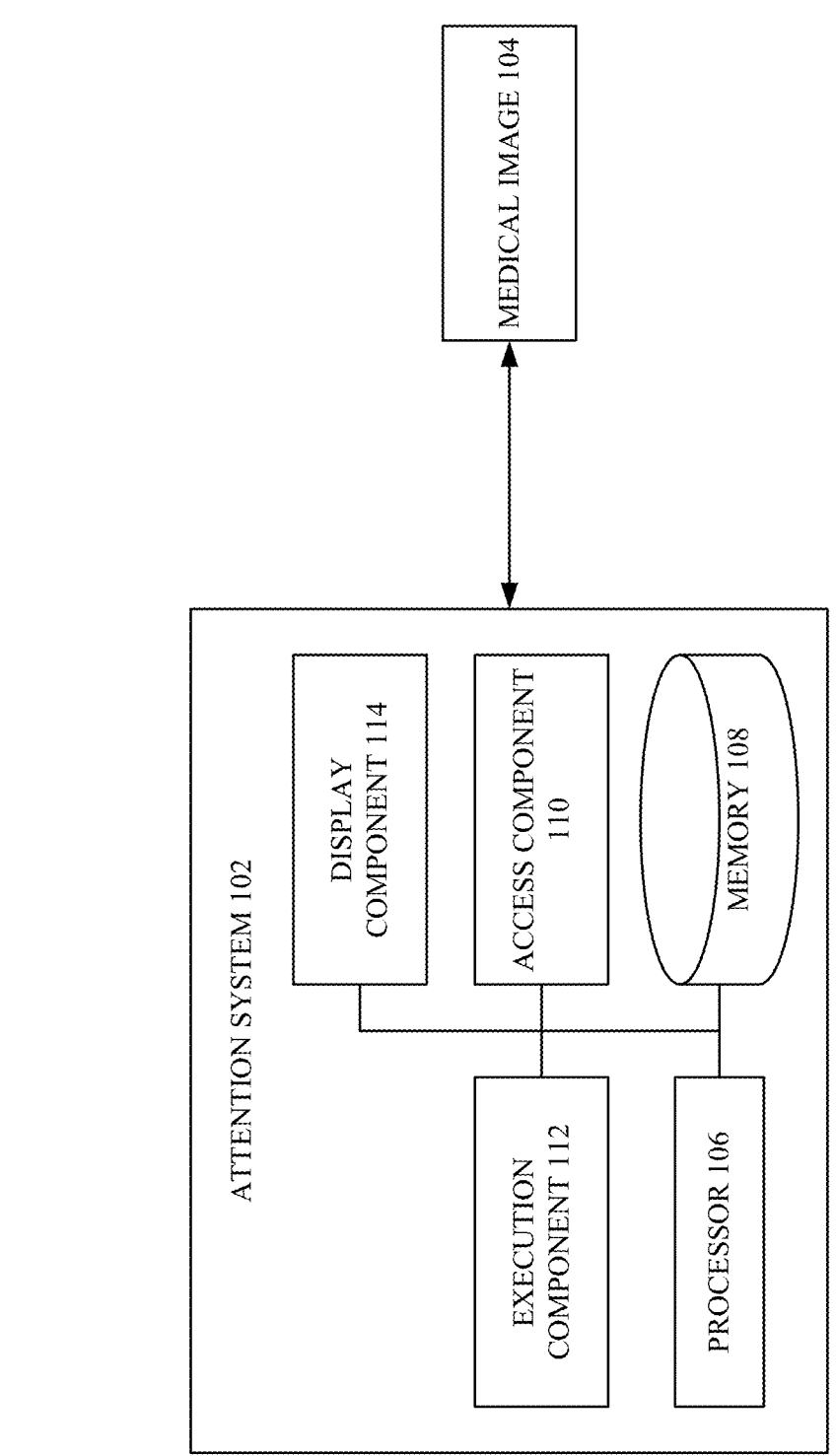
FIG. 1 illustrates a block diagram of an example, non-limiting system that facilitates explainable visual attention for deep learning in accordance with one or more embodiments described herein.

The following detailed description is merely illustrative and is not intended to limit embodiments or application/uses of embodiments. Furthermore, there is no intention to be bound by any expressed or implied information presented in the preceding Background or Summary sections, or in the Detailed Description section.

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

A deep learning neural network can be trained (e.g., in supervised fashion, in unsupervised fashion, in reinforcement learning fashion) to perform an inferencing task (e.g., classification, segmentation, regression) on a medical image (e.g., on a computed tomography (CT) scanned image, on a magnetic resonance imaging (MRI) scanned image, on an X-ray scanned image, on an ultrasound scanned image, on a positron emission tomography (PET) scanned image). During or otherwise to facilitate performance of the inferencing task, it can be desired for the deep learning neural network to pay closer attention to certain portions of the medical image than to other portions of the medical image. After all, it can be the case that not every depicted region of the medical image is dispositive or otherwise important with respect to the inferencing task. Accordingly, the inferencing task can be accurately or precisely performed by focusing mainly on whatever regions of the medical image are task-dispositive and by downplaying or ignoring whatever other regions of the medical image are not task-dispositive.

Existing techniques attempt to accomplish such attention or focus by outfitting the deep learning neural network with learnable attention blocks. A learnable attention block is one or more hidden layers that follow an upstream portion of the deep learning neural network and that precede a downstream portion of the deep learning neural network, such that the learnable attention block receives various feature/activation maps that are computed by the upstream portion, such that the learnable attention block computes a respective attention score (also referred to as an alignment score) for each of those various feature/activation maps, and such that the downstream portion respectively weights those various feature/activation maps by the computed attention scores so as to compute its own feature/activation maps. Accordingly, the learnable attention block can be considered as determining relative levels of importance for the various feature/activation maps received from the upstream portion (e.g., a feature/activation map for which a numerically low attention score is computed can be considered as less important; a feature/activation map for which a numerically high attention score is computed can be considered as more important). In other words, the upstream portion can compute various feature/activation maps, the learnable attention block can determine which of those various feature/activation maps are more or less significant, and the downstream portion can focus on whichever of those various feature/activation maps are determined to be more significant.

Unfortunately, such existing techniques exhibit insufficient interpretability or explainability. Such lack of interpretability or explainability is due, at least in part, to various reasons.

First, the attention scores of existing techniques are entirely hidden within the deep learning neural network. In other words, when existing techniques are implemented, the attention scores that are computed by a learnable attention block are not provided or otherwise treated as independent outputs of the deep learning neural network. Accordingly, a user or technician of the deep learning neural network is not made aware of such attention scores at all, meaning that the user or technician is not apprised of where the deep learning neural network focused its attention when performing the inferencing task on the medical image.

Second, even if the attention scores of existing techniques were to be extracted and provided as independent outputs of the deep learning neural network, such attention scores carry no readily-understandable semantic meaning with respect to the medical image. Indeed, as mentioned above, the learnable attention block is sandwiched between an upstream portion and a downstream portion of the deep learning neural network, and the attention scores computed by that learnable attention block serve as weights for respective feature/activation maps that are generated by the upstream portion. Accordingly, the attention scores can be considered as indicating which of those feature/activation maps are to receive more or less focus from the deep learning neural network. Unfortunately, however, it is not at all clear how such feature/activation maps relate to the medical image. After all, such feature/activation maps are hidden, abstract, numerical representations (e.g., latent vectors) that have no readily-identifiable or interpretable physical meaning with respect to the medical image. So, even if a user or technician of the deep learning neural network were made aware of the attention scores computed by the learnable attention block, such attention scores would not convey to the user or technician any physically-relevant information regarding the medical image. Instead, such attention scores would only identify for the user or technician those various feature/activation maps to which the deep learning neural network is paying more or less attention; such information can be considered as tantamount to useless since those feature/activation maps bear no easily-understood relationship to whatever visual content is depicted in the medical image.

Third, even if the attention scores of existing techniques were to carry some physically-relevant meaning with respect to the medical image, such physically-relevant meaning would be layer-dependent or relative, rather than layer-transcendent or absolute. Again, the learnable attention block receives multiple feature/activation maps from the upstream portion of the deep learning neural network and assigns a respective attention score to those received feature/activation maps. Note that different layers of the deep learning neural network can produce different numbers of, different sizes of, different formats of, or different types of feature/activation maps. Accordingly, the intra-network depth at which the learnable attention block is located (e.g., can be located more toward the upstream side of the deep learning neural network, or can be located more toward the downstream side of the deep learning neural network) dictates how many and what types of feature/activation maps are assigned attention scores by the learnable attention block, which commensurately dictates the meanings (if any) of the computed attention scores. This can be considered as confusing for users or technicians, since the meaning of attention scores can thus vary across neural networks that have differently-located learnable attention blocks (e.g., suppose that two separate neural networks with differently-located learnable attention blocks are trained to perform the inferencing task; in such case, attention scores produced by one neural network will not have the same substantive meaning as attention scores produced by the other neural network).

Fourth, learnable attention blocks of existing techniques are unguided and thus are vulnerable to learning strange or undesirable attention patterns. In particular, when existing techniques are implemented, ground-truth attention scores are not used to directly train the learnable attention block. Instead, the learnable attention block is updated via back-propagation with the rest of the deep learning neural network (e.g., so as to minimize a final error with respect to a ground-truth inferencing task result, so as to maximize a final reinforcement learning reward). Such lack of ground-truth attention scores can be at least partially due to the above-mentioned fact that attention scores of existing techniques carry no readily-interpretable physical meaning (e.g., it cannot be known in advance what ground-truth attention score should correspond to a given feature/activation map when that given feature/activation map has no clear physical meaning). Such unguided training can ultimately cause the learnable attention block to become overfitted or to otherwise learn to assign attention scores in weird, unexpected, or inexplicable fashions. Again, this undermines the interpretability or explainability of existing techniques.

Accordingly, systems or techniques that can facilitate deep learning attention for medical images with heightened interpretability or explainability can be desirable.

Various embodiments described herein can address one or more of these technical problems. One or more embodiments described herein can include systems, computer-implemented methods, apparatus, or computer program products that can facilitate explainable visual attention for deep learning. In particular, various embodiments described herein can involve configuring or training a deep learning neural network to perform an inferencing task on an inputted medical image, where the deep learning neural network can comprise a primary processing channel and an auxiliary processing channel that branches off from the primary processing channel. As described herein, the primary processing channel can be responsible for generating as output an inferencing task result for the inputted medical image, whereas the auxiliary processing channel can instead be responsible for generating as output an attention map for the inputted medical image. In various aspects, the attention map can indicate or represent pixel-wise (or voxel-wise) attention scores for the inputted medical image. In other words, the attention map can be considered as indicating how important or unimportant the deep learning neural network believes or infers each individual pixel (or each individual voxel) of the inputted medical image is for performance of the inferencing task. In still other words, the attention map can be considered as identifying or indicating to which pixels (or voxels) of the inputted medical image the deep learning neural network is focusing its attention. In various instances, as described herein, the auxiliary processing channel can be trained in supervised fashion using training medical images and respectively-corresponding ground-truth attention maps, and the primary processing channel can be trained using a loss function that is weighted in pixel-wise (or voxel-wise) fashion by such ground-truth attention maps. In various cases, such ground-truth attention maps can be obtained based on executing any suitable edge detector or boundary detector on the training medical images. In various other cases (e.g., for image-to-image regression tasks), such ground-truth attention maps can instead be obtained based on differences between the training medical images and respectively corresponding ground-truth inferencing task results. In still other cases, such ground-truth attention maps can instead be obtained based on uncertainties or errors that the deep learning neural network exhibited with respect to the training medical images during previous training epochs.

Various embodiments described herein can be considered as facilitating visual attention with heightened explainability or interpretability as compared to existing techniques.

First, as mentioned above, the attention scores of existing techniques are entirely hidden. That is, such attention scores are not provided or extracted as independent outputs that are viewable by a user or technician. In stark contrast, the attention map described herein is provided as an independent output that is viewable by a user or technician. Accordingly, when various embodiments described herein are implemented, the user or technician can become informed of where the deep learning neural network focuses its attention when performing the inferencing task on the medical image.

Second, as mentioned above, the attention scores of existing techniques possess no readily-interpretable physical meaning with respect to the medical image. After all, such attention scores correspond to (e.g., are used to internally weight) various feature/activation maps that are internally computed by hidden neural network layers, and such various feature/activation maps are abstract latent vectors that possess no easily-understood physical or semantic relationship to the visual content depicted in the medical image. In stark contrast, the attention map described herein possesses a readily-interpretable physical meaning with respect to the medical image. Specifically, the attention map described herein indicates a respective attention score for each individual pixel (or each individual voxel) of the medical image. Thus, the attention map can be considered as indicating which specific pixels (or voxels) of the medical image are determined by the deep learning neural network to be more or less important for performance of the inferencing task. Accordingly, the attention map can be visually rendered (e.g., like a heat map) so as to visually emphasize pixels (or voxels) of the medical image that are receiving more attention or focus from the deep learning neural network. Such direct relationship to the individual pixels (or voxels) of the medical image imbues the attention map described herein with clear, physically-relevant meaning, which makes the attention map easily understandable, interpretable, or explainable.

Third, as mentioned above, the attention scores of existing techniques are layer-dependent. After all, even if at least some substantive meaning were to be gleaned from such attention scores, such substantive meaning would depend upon the particular characteristics of the feature/activation maps that those attention scores weight, and different neural network layers (e.g., layers located at different intra-network depths) produce feature/activation maps with different characteristics. Accordingly, distinct neural networks that are configured to perform the inferencing task but that have differently-located learnable attention blocks would produce attention scores that have inconsistent and thus incomparable meanings, which is confusing for users or technicians (e.g., one network might compute attention scores for feature/activation maps produced by an a-th hidden layer, whereas a different network might compute attention scores for feature/activation maps produced by a b-th hidden layer, for any suitable positive integers a>b>1; thus, such attention scores could not appropriately be compared with each other). In stark contrast, the attention map described herein indicates pixel-wise (or voxel-wise) attention scores, no matter the intra-network depth at which the auxiliary processing channel is located. Indeed, although the specific construction of one or more layers of the auxiliary processing channel might have to be adjusted depending upon the intra-network depth at which the auxiliary processing channel branches off from the primary processing channel, the output of the auxiliary processing channel, as described herein, is always a pixel-wise (or voxel-wise) map of attention scores. Accordingly, distinct neural networks that are configured to perform the inferencing task but that have differently-located auxiliary processing channels would nevertheless produce attention maps that have consistent and thus comparable meanings, which reduces confusion for users or technicians (e.g., each network would produce a respective pixel-wise (or voxel-wise) map of attention scores, and so such maps could appropriately be compared with each other).

Fourth, as mentioned above, the learnable attention blocks of existing techniques are unguided by ground-truth attention scores. Such lack of guidance can cause such learnable attention blocks to learn to assign attention is strange or inexplicable ways. In stark contrast, the auxiliary processing channel described herein can be trained based on training medical images and respectively corresponding ground-truth attention maps. Such ground-truth attention maps (which can be used to dynamically weight a training loss function of the primary processing channel) can be obtained via edge detection, uncertainty quantification, or image-annotation difference computation, as described herein. In any case, the use of such ground-truth attention maps can reduce the likelihood of the auxiliary processing channel learning to assign attention in unusual, strange, or inexplicable fashions.

For at least these reasons, various embodiments described herein can be considered as facilitating visual deep learning attention with improved explainability.

Various embodiments described herein can be considered as a computerized tool (e.g., any suitable combination of computer-executable hardware or computer-executable software) that can facilitate explainable visual attention for deep learning. In various aspects, such computerized tool can comprise an access component, an execution component, or a display component.

In various embodiments, there can be a particular medical image. In various aspects, the particular medical image can exhibit any suitable format, size, or dimensionality (e.g., the particular medical image can be a two-dimensional pixel array, or the particular medical image can be a three-dimensional voxel array). In various instances, the particular medical image can be generated or captured by any suitable medical imaging modality or equipment (e.g., generated or captured by a CT scanner, by an MRI scanner, by an X-ray scanner, by an ultrasound scanner, or by a PET scanner). In various cases, the particular medical image can visually depict any suitable anatomical structure of any suitable medical patient.

In various aspects, an inferencing task can be performable on the particular medical image. In various instances, the inferencing task can be any suitable predictive computation or functionality that is applicable to images. As some non-limiting examples, the inferencing task can be image classification, image segmentation, or image-to-image regression. In various aspects, the inferencing task can be considered as having some diagnostic or prognostic relevance with respect to the anatomical structure depicted in the particular medical image.

In any case, it can be desired to perform the inferencing task on the particular medical image. Furthermore, it can be desired to discover which pixels (or voxels) of the particular medical image are receiving more or less attention or focus during such performance (e.g., to discover which pixels (or voxels) of the particular medical image are more or less dispositive with respect to the inferencing task). In various aspects, the computerized tool described herein can facilitate such objectives.

In various embodiments, the access component of the computerized tool can electronically receive or otherwise electronically access the particular medical image. In some aspects, the access component can electronically retrieve the particular medical image from any suitable centralized or decentralized data structures (e.g., graph data structures, relational data structures, hybrid data structures), whether remote from or local to the access component. In any case, the access component can electronically obtain or access the particular medical image, such that other components of the computerized tool can electronically interact with (e.g., read, write, edit, copy, manipulate) the particular medical image.

In various embodiments, the execution component of the computerized tool can electronically store, maintain, control, or otherwise access a deep learning neural network. In various aspects, the deep learning neural network can comprise a primary processing channel and an auxiliary processing channel.

In various instances, the primary processing channel can exhibit any suitable deep learning internal architecture. For example, the primary processing channel can include any suitable numbers of any suitable types of layers (e.g., input layer, one or more hidden layers, output layer, any of which can be convolutional layers, dense layers, non-linearity layers, pooling layers, batch normalization layers, or padding layers). As another example, the primary processing channel can include any suitable numbers of neurons in various layers (e.g., different layers can have the same or different numbers of neurons as each other). As yet another example, the primary processing channel can include any suitable activation functions (e.g., softmax, sigmoid, hyperbolic tangent, rectified linear unit) in various neurons (e.g., different neurons can have the same or different activation functions as each other). As still another example, the primary processing channel can include any suitable interneuron connections or interlayer connections (e.g., forward connections, skip connections, recurrent connections).

In various cases, the auxiliary processing channel can likewise exhibit any suitable deep learning internal architecture. For example, the auxiliary processing channel can include any suitable numbers of any suitable types of layers (e.g., input layer, one or more hidden layers, output layer, any of which can be convolutional layers, dense layers, non-linearity layers, pooling layers, batch normalization layers, or padding layers). As another example, the auxiliary processing channel can include any suitable numbers of neurons in various layers (e.g., different layers can have the same or different numbers of neurons as each other). As yet another example, the auxiliary processing channel can include any suitable activation functions (e.g., softmax, sigmoid, hyperbolic tangent, rectified linear unit) in various neurons (e.g., different neurons can have the same or different activation functions as each other). As still another example, the auxiliary processing channel can include any suitable interneuron connections or interlayer connections (e.g., forward connections, skip connections, recurrent connections).

In various aspects, the auxiliary processing channel can branch off from the primary processing channel, such that the auxiliary processing channel is in parallel with at least some portion of the primary processing channel. For instance, the primary processing channel can have a given hidden layer between its input layer and its output layer, and an input layer of the auxiliary processing channel can be configured to receive as input whatever feature/activation maps are produced by that given hidden layer, such that the auxiliary processing channel is in parallel with all of the layers of the primary processing channel that are downstream of that given hidden layer.

In any case, the primary processing channel can be configured to perform the inferencing task on inputted medical images, whereas the auxiliary processing channel can instead be configured to generate pixel-wise (or voxel-wise) attention maps for such inputted medical images. Accordingly, the execution component can electronically execute the deep learning neural network on the particular medical image, and such execution can yield an inferencing task result and an attention map. More specifically, the execution component can feed the particular medical image to an input layer of the primary processing channel, the particular medical image can complete a forward pass through one or more hidden layers of the primary processing channel, and such forward pass can cause an output layer of the primary processing channel to compute the inferencing task result. Furthermore, an input layer of the auxiliary processing channel can receive one or more activations from whichever hidden layer of the primary processing channel at which the auxiliary processing channel branches off, such one or more activations can complete a forward pass through one or more hidden layers of the auxiliary processing channel, and such forward pass can cause an output layer of the auxiliary processing channel to compute the attention map.

In various aspects, the inferencing task result can be whatever computational result that the primary processing channel determines or predicts for the particular medical image. Accordingly, the inferencing task result can be any suitable electronic data whose format, size, or dimensionality depends upon the inferencing task that the primary processing channel is configured to perform. As a non-limiting example, if the inferencing task is image classification, then the inferencing task result can be a classification label that the primary processing channel has predicted for the particular medical image. As another non-limiting example, if the inferencing task is image segmentation, then the inferencing task result can be a segmentation mask that the primary processing channel has predicted for the particular medical image. As yet another non-limiting example, if the inferencing task is image-to-image regression (e.g., denoising, resolution enhancement, modality transformation), then the inferencing task result can be a regressed version (e.g., a denoised version, a resolution-enhanced version, a modality-transformed version) of the particular medical image that the primary processing channel has predicted.

In various instances, the attention map can be a pixel-wise (or voxel-wise) array of attention scores that corresponds to the particular medical image, where each attention score can be a scalar weight whose magnitude indicates a level of attention, focus, importance, or significance that a respective pixel (or voxel) of the particular medical image has with regard to the inferencing task (e.g., an attention score can be a decimal varying continuously or discretely from 0 to 1, with 0 indicating no importance with respect to the inferencing task and with 1 indicating high importance with respect to the inferencing task). For instance, if the attention map indicates that a given pixel (or voxel) of the particular medical image has a low-magnitude attention score (e.g., close to 0), this can be interpreted to mean that the given pixel (or voxel) does not heavily influence or contribute to disposition of the inferencing task. On the other hand, if the attention map instead indicates that the given pixel (or voxel) of the particular medical image has a high-magnitude attention score (e.g., close to 1), this can be interpreted to mean that the given pixel (or voxel) heavily influences or contributes to disposition of the inferencing task. Put another way, the attention map can be considered as a prediction identifying how much or how little each individual pixel (or voxel) of the particular medical image is paid attention to by the primary processing channel. In any case, the attention map can be considered as having or exhibiting clear and easily-understandable physical, semantic, or substantive meaning with respect to the particular medical image (e.g., the particular medical image depicts some visual content, and the attention map shows in pixel-wise (or voxel-wise) fashion which portions or regions of such visual content are more or less task-dispositive).

In this way, the primary processing channel can be considered as performing the inferencing task on the particular medical image, and the auxiliary processing channel can be considered as predicting or inferring which specific pixels (or voxels) of the particular medical image will be paid more or less attention to by the primary processing channel.

In various embodiments, the display component of the computerized tool can electronically render, on any suitable electronic display, the inferencing task result or the attention map, such that the inferencing task result or the attention map are viewable by a user or technician of the computerized tool. In this way, the user or technician can be apprised of not only the inferencing task result, but also of which individual pixels (or voxels) of the particular medical image contributed most to the inferencing task result.

Note that, in various aspects, the attention map can be leveraged by the user or technician for failure analysis of the inferencing task result. As a non-limiting example, suppose that the user or technician decides that the inferencing task result is incorrect. That is, the user or technician can conclude that the primary processing channel inaccurately performed the inferencing task on the particular medical image. In such case, the attention map can be helpful in determining how or why the primary processing channel inaccurately performed the inferencing task. Indeed, the attention map might show that some unexpected pixels (or voxels) of the particular medical image received disproportionately high attention or focus. This can indicate that the primary processing channel was distracted or otherwise thrown-off by whatever visual content is illustrated by those unexpected pixels (or voxels). In other words, the attention map can help to reveal insights regarding visual characteristics to which the primary processing channel is not agnostic but to which the primary processing channel is supposed to be agnostic. Accordingly, the user or technician can utilize such insights to help retrain or fine-tune the primary processing channel so as to avoid similar failures in the future.

To help cause the inferencing task result and the attention map to be accurate (e.g., to help cause the primary processing channel to correctly perform the inferencing task on inputted medical images, and to help cause the auxiliary processing channel to correctly predict which pixels (or voxels) of such inputted medical images are more or less important with respect to the inferencing task), the deep learning neural network can first undergo training. In various aspects, the access component can receive, retrieve, or otherwise access an annotated training dataset, and the computerized tool can comprise a training component that can train the deep learning neural network on the annotated training dataset.

In various aspects, the annotated training dataset can include a set of training medical images. In various instances, a training medical image can be any suitable medical image having the same size, format, or dimensionality (e.g., the same number or arrangement of pixels (or voxels)) as the particular medical image. In various cases, the annotated training dataset can also include a set of ground-truth inferencing task results that respectively correspond to the set of training medical images. In various aspects, a ground-truth inferencing task result can be a correct or accurate inferencing task result (e.g., correct or accurate classification label, correct or accurate segmentation mask, correct or accurate regression output) that is known or deemed to correspond to a respective training medical image. In various instances, the annotated training dataset can further include a set of ground-truth attention maps that respectively correspond to the set of training medical images. In various cases, a ground-truth attention map can be a correct or accurate array of pixel-wise or voxel-wise attention scores that are known or deemed to correspond to a respective training medical image.

In some embodiments, a ground-truth attention map for a given training medical image can be obtained by executing an edge/boundary detector on the given training medical image. Indeed, it can be the case that visually perceptible edges, boundaries, or other contours (e.g., of anatomical structures) that are illustrated in the given training medical image are known or deemed to be highly relevant or otherwise dispositive with respect to the inferencing task. Accordingly, whatever pixels (or voxels) of the given training medical image that make up or otherwise belong to those visually perceptible edges, boundaries, or other contours can be assigned higher ground-truth attention scores. To accomplish this, any suitable edge/boundary detector can be implemented. In particular, the edge/boundary detector can be any suitable machine learning model that is pre-trained via any suitable training paradigm (e.g., supervised training, unsupervised training, reinforcement learning) to segment, within an inputted image, whatever pixels (or voxels) that it infers or determines belong to an edge, boundary, or contour of that inputted image. So, the edge/boundary detector can be executed on the given training medical image; such execution can yield an inferred segmentation mask that indicates which pixels (or voxels) of the given training medical image belong to edges, boundaries, or contours that are visually illustrated in the given training medical image; and such inferred segmentation mask can be treated or otherwise taken as the ground-truth attention map for the given training medical image.

In other embodiments, the ground-truth attention map for the given training medical image can instead be obtained by comparing the given training medical image to a ground-truth inferencing task result that corresponds to the given training medical image. Indeed, if the inferencing task is image-to-image regression, then the ground-truth inferencing task result can be an image of the same size, format, or dimensionality as the given training medical image; in fact, the ground-truth inferencing task result can be a regressed version (e.g., denoised version, resolution-enhanced version, modality-transformed version) of the given training medical image. In such situations, it can be the case that the intensity values (e.g., Hounsfield units) of some pixels (or voxels) of the given training medical image undergo little or no change when being converted to the ground-truth inferencing task result, and it can be the case that the intensity values of other pixels (or voxels) of the given training medical image undergo significant change when being converted to the ground-truth inferencing task result. Accordingly, whatever pixels (or voxels) of the given training medical image that undergo significant change in the generation of the ground-truth inferencing task result can be assigned higher ground-truth attention scores. To accomplish this, a difference array can be computed by applying matrix subtraction between the given training medical image and the ground-truth inferencing task result, that difference array can be normalized, and an absolute value of that normalized difference array can be treated or otherwise taken as the ground-truth attention map for the given training medical image.

In yet other embodiments, the ground-truth attention map for the given training medical image can instead be obtained by quantifying uncertainty or error exhibited by the primary processing channel with respect to the given training medical image. In particular, it can be the case that the primary processing channel was previously executed (e.g., during a prior training epoch) on the given training medical image. If the inferencing task is image segmentation or image-to-image regression, such previous execution can have yielded an output array. That output array can be considered as the previously-predicted segmentation mask or the previously-predicted regressed image that the primary processing channel believed corresponded to the given training medical image. In contrast, the ground-truth inferencing task result can be considered as the correct or accurate segmentation mask or regressed image that is known or deemed to correspond to the given training medical image. Now, it can be the case that the intensity values of some pixels (or voxels) of the output array are close to what the ground-truth inferencing task result indicates that they should be, and it can be the case that the intensity values of other pixels (or voxels) of the output array are far from what the ground-truth inferencing task result indicates that they should be. Accordingly, whatever pixels (or voxels) of the output array (and thus of the given training medical image by proxy) that are significantly different from what the ground-truth inferencing task result indicates can be assigned higher ground-truth attention scores. To accomplish this, a difference array can be computed by applying matrix subtraction between the output array and the ground-truth inferencing task result, that difference array can be normalized, and an absolute value of that normalized difference array can be treated or otherwise taken as the ground-truth attention map for the given training medical image.

In any case, the training component can train the deep learning neural network on the annotated training dataset, as follows. Prior to the start of such training, the trainable internal parameters (e.g., weight matrices, bias vectors, convolutional kernels) of the deep learning neural network (e.g., of the primary processing channel, of the auxiliary processing channel) can be randomly initialized.

In various aspects, the training component can select from the annotated training dataset any suitable training medical image, any suitable respectively corresponding ground-truth inferencing task result, and any suitable respectively corresponding ground-truth attention map. In various instances, the training component can execute the deep learning neural network on the selected training medical image, thereby causing the primary processing channel to produce a first output and causing the auxiliary processing channel to produce a second output.

More specifically, the training component can feed the selected training medical image to the input layer of the primary processing channel, the selected training medical image can complete a forward pass through the one or more hidden layers of the primary processing channel, and such forward pass can cause the output layer of the primary processing channel to compute the first output. Furthermore, the input layer of the auxiliary processing channel can receive one or more activations from whichever hidden layer of the primary processing channel at which the auxiliary processing channel branches off, such one or more activations can complete a forward pass through the one or more hidden layers of the auxiliary processing channel, and such forward pass can cause the output layer of the auxiliary processing channel to compute the second output.

Note that the format, size, or dimensionality of the first output can be controlled or otherwise dictated by the number, arrangement, or sizes of the neurons or of other internal parameters (e.g., convolutional kernels) that are contained in or that otherwise make up the output layer of the primary processing channel. So, the first output can be forced to have whatever format, size, or dimensionality that is suitable for the inferencing task, by adding, removing, or otherwise adjusting neurons or other internal parameters to, from, or within the output layer of the primary processing channel. Accordingly, the first output can be considered as the predicted inferencing task result (e.g., predicted classification label, predicted segmentation mask, predicted regression output) that the primary processing channel believes should correspond to the selected training medical image. In contrast, the selected ground-truth inferencing task result can be the correct or accurate inferencing task result (e.g., correct or accurate classification label, correct or accurate segmentation mask, correct or accurate regression output) that is known or deemed to correspond to the selected training medical image. In various cases, if the primary processing channel has so far undergone no or little training, the first output can be highly inaccurate (e.g., can be very different from the selected ground-truth inferencing task result).

Likewise, note that the format, size, or dimensionality of the second output can be controlled or otherwise dictated by the number, arrangement, or sizes of the neurons or of other internal parameters (e.g., convolutional kernels) that are contained in or that otherwise make up the output layer of the auxiliary processing channel. Thus, the second output can be forced to have any desired format, size, or dimensionality by adding, removing, or otherwise adjusting neurons or other internal parameters to, from, or within the output layer of the auxiliary processing channel. Accordingly, the second output can be considered as the predicted attention map (e.g., predicted array of pixel-wise (or voxel-wise) attention scores) that the auxiliary processing channel believes should correspond to the selected training medical image. In contrast, the selected ground-truth attention map can be the correct or accurate attention map (e.g., correct or accurate array of pixel-wise (or voxel-wise) attention scores) that is known or deemed to correspond to the selected training medical image. In various cases, if the auxiliary processing channel has so far undergone no or little training, the second output can be highly inaccurate (e.g., can be very different from the selected ground-truth attention map).

In any case, the training component can compute a first error or loss (e.g., mean absolute error (MAE), mean squared error (MSE), cross-entropy error) between the first output and the selected ground-truth inferencing task result. In various aspects, the training component can weight the first error or loss in pixel-wise (or voxel-wise) fashion according to the selected ground-truth attention map (e.g., can be accomplished via point-wise multiplication and summing), and the training component can update the internal parameters of the primary processing channel by performing backpropagation (e.g., stochastic gradient descent) driven by the first error or loss as weighted by the selected ground-truth attention map.

Similarly, the training component can compute a second error or loss (e.g., MAE, MSE, cross-entropy error) between the second output and the selected ground-truth attention map, and the training component can update the internal parameters of the auxiliary processing channel by performing backpropagation (e.g., stochastic gradient descent) driven by the second error or loss.

In various aspects, such training procedure can be repeated for any suitable number of training medical images. Such training can ultimately cause the trainable internal parameters of the primary processing channel to become iteratively optimized for accurately performing the inferencing task on inputted medical images, and such training can also ultimately cause the trainable internal parameters of the auxiliary processing channel to become iteratively optimized for accurately predicting how important individual pixels (or voxels) of such inputted medical images are with respect to the inferencing task.

Various embodiments described herein can be employed to use hardware or software to solve problems that are highly technical in nature (e.g., to facilitate explainable visual attention for deep learning), that are not abstract and that cannot be performed as a set of mental acts by a human. Further, some of the processes performed can be performed by a specialized computer (e.g., deep learning neural networks having internal parameters such as convolutional kernels) for carrying out defined acts related to deep learning. For example, such defined acts can include: accessing, by a device operatively coupled to a processor, a medical image generated by a medical imaging scanner; and performing, by the device and via execution of a deep learning neural network, an inferencing task on the medical image, wherein the deep learning neural network receives as input the medical image and produces as output both an inferencing task result and an attention map indicating on which pixels or voxels of the medical image the deep learning neural network focused in generating the inferencing task result.

Such defined acts are not performed manually by humans. Indeed, neither the human mind nor a human with pen and paper can electronically access a scanned medical image (e.g., X-ray image, MRI image, CT image) and electronically perform an inferencing task by executing a neural network on the scanned medical image, where the neural network computes as output both an inferencing task result (e.g., classification label, segmentation mask, regressed image) and an attention map showing on which specific pixels (or voxels) of the scanned medical image the neural network focused (e.g., which specific pixels (or voxels) contributed most heavily to the inferencing task result). Indeed, a neural network is an inherently-computerized construct that simply cannot be meaningfully executed or trained in any way by the human mind without computers. A computerized tool that can execute a neural network on a scanned medical image is likewise inherently-computerized and cannot be implemented in any sensible, practical, or reasonable way without computers.

Moreover, various embodiments described herein can integrate into a practical application various teachings relating to explainable visual attention for deep learning. As described above, existing techniques incorporate learnable attention blocks into neural networks, where such learnable attention blocks compute attention scores that are used to weight respective hidden activation maps. Unfortunately, such learnable attention blocks suffer from a lack of explainability or interpretability. Indeed, the attention scores provided by such learnable attention blocks are entirely hidden (e.g., not extracted as stand-alone neural network outputs) and possess no readily-understandable physical meaning. Moreover, even if some physical meaning were to be gleaned from such attention scores, such meaning would depend upon the intra-network depths at which the learnable attention blocks are located. Furthermore, such learnable attention blocks are trained in an unguided fashion that can cause strange or unexplainable attention patterns to be learned.

In stark contrast, various embodiments described herein can address one or more of these technical problems. In particular, various embodiments described herein involve training or configuring a neural network to receive as input a medical image and to produce two distinct outputs: an inferencing task result for the inputted medical image; and an attention map indicating relative levels of importance or unimportance with respect to the inferencing task result for each individual pixel (or voxel) of the inputted medical image. In various aspects, the inferencing task result can be produced by a primary processing channel of the neural network, and the attention map can be produced by an auxiliary processing channel that branches off from, and is in parallel with some downstream portion of, the primary processing channel.

Unlike the attention scores of existing techniques, the attention map described herein is provided or otherwise treated as a separate, distinct output of the neural network (e.g., a user or technician is not apprised of the attention scores of existing techniques, but the user or technician is apprised of the attention map described herein).

Also unlike the attention scores of existing techniques, the attention map described herein carries easily-apparent physical or semantic meaning. For example, each weight in the attention map shows how important or unimportant a respective pixel (or voxel) of the inputted medical image is with respect to the inferencing task result, and such importance or unimportance is meaningful since it is clear how that pixel (or voxel) relates to the visual content of the inputted medical image. In contrast, each attention score of existing techniques shows only how important or unimportant a respective hidden activation map is, and such importance or unimportance is not meaningful since it is unclear how that hidden activation map relates to the visual content of the inputted medical image (e.g., the hidden activation map is an abstract representation or latent vector with no apparent or interpretable meaning).

Additionally, unlike the attention scores of existing techniques, the meaning of the attention map described herein is not layer-dependent. Indeed, whatever meaning (if any) of the attention scores computed by a learnable attention block depends upon where the learnable attention block is located within the neural network (e.g., the learnable attention block produces attention scores for whatever hidden activation maps that it receives as input; different hidden layers produce different quantities, types, or formats of hidden activation maps; accordingly, differently-located learnable attention blocks would produce different quantities of attention scores with different meanings). In contrast, the attention map described herein indicates the importance, attention, or focus of each pixel (or voxel) of the inputted medical image, no matter the intra-network depth at which the auxiliary processing channel is located (e.g., no matter the depth at which the auxiliary processing channel is located, the auxiliary processing channel can be appropriately configured to produce a pixel-wise (or voxel-wise) array of attention scores).

Furthermore, unlike the learnable attention blocks of existing techniques, the auxiliary processing channel described herein can be trained in guided fashion using ground-truth attention maps. Indeed, ground-truth attention scores can be unavailable or unobtainable for existing techniques, precisely because such attention scores are devoid of clear physical meaning (e.g., if it is not known a priori what a training hidden activation map means or represents, it surely cannot be known what ground-truth attention score should correspond to that training hidden activation map). In contrast, ground-truth attention maps can be obtained to train the auxiliary processing channel, since it can be known or estimated a priori how important or unimportant each pixel (or voxel) of a training medical image is with respect to the inferencing task (e.g., as described herein, such ground-truth attention maps can be obtained via edge/boundary detection, via image-annotation comparison, or via past uncertainty/error quantification).

Further still, the attention map described herein can be leveraged for failure analysis of the neural network in ways that the attention scores of existing techniques cannot. Indeed, suppose that the primary processing channel incorrectly or inaccurately generates the inferencing task result. In such case, a potential reason or explanation for such inaccuracy can be gleaned from the attention map produced by the auxiliary processing channel (e.g., the attention map might show that certain pixels (or voxels) of the inputted medical image were unexpectedly or wrongly emphasized or considered important by the primary processing channel). In this way, the attention map can be leveraged so as to identify insights such as visual characteristics or artefacts that distracted or threw-off the primary processing channel, and such insights can be useful for subsequently retraining or fine-tuning the primary processing channel.

For at least these reasons, various embodiments described herein facilitate visual attention of medical images for deep learning with heightened or increased explainability, as compared to existing techniques. Thus, various embodiments described herein certainly constitute a tangible and concrete technical improvement or technical advantage in the field of deep learning. Accordingly, such embodiments clearly qualify as useful and practical applications of computers.

Furthermore, various embodiments described herein can control real-world tangible devices based on the disclosed teachings. For example, various embodiments described herein can electronically train or execute real-world deep learning neural networks on real-world images (e.g., X-ray scanned images, CT scanned images), and can electronically render real-world results (e.g., classification labels, segmentation masks, regressed images, attention maps) on real-world computer screens.

It should be appreciated that the herein figures and description provide non-limiting examples of various embodiments and are not necessarily drawn to scale.

FIG. 1 illustrates a block diagram of an example, non-limiting system 100 that can facilitate explainable visual attention for deep learning in accordance with one or more embodiments described herein. As shown, an attention system 102 can be electronically integrated, via any suitable wired or wireless electronic connections, with a medical image 104.

In various embodiments, the medical image 104 can be any suitable image exhibiting any suitable format, size, or dimensionality. As a non-limiting example, the medical image 104 can be an x-by-y array of pixels, for any suitable positive integers x and y. As another non-limiting example, the medical image 104 can be an x-by-y-by-z array of voxels, for any suitable positive integers x, y, and z. In various aspects, the medical image 104 can be captured or otherwise generated by any suitable medical imaging modality. As a non-limiting example, the medical image 104 can be captured or generated by a CT scanner, in which case the medical image 104 can be considered as a CT scanned image. As another non-limiting example, the medical image 104 can be captured or generated by an MRI scanner, in which case the medical image 104 can be considered as an MRI scanned image. As yet another non-limiting example, the medical image 104 can be captured or generated by an X-ray scanner, in which case the medical image 104 can be considered as an X-ray scanned image. As even another non-limiting example, the medical image 104 can be captured or generated by an ultrasound scanner, in which case the medical image 104 can be considered as an ultrasound scanned image. As still another non-limiting example, the medical image 104 can be captured or generated by a PET scanner, in which case the medical image 104 can be considered as a PET scanned image. In various instances, the medical image 104 can have undergone any suitable image reconstruction techniques, such as filtered back projection.

In various aspects, the medical image 104 can visually depict or illustrate any suitable anatomical structure of any suitable medical patient (e.g., human, animal, or otherwise). In various instances, the anatomical structure can be any suitable bodily organ of the medical patient, any suitable bodily tissue of the medical patient, any suitable body part of the medical patient, any suitable bodily fluid of the medical patient, any suitable bodily cavity of the medical patient, any suitable surgical implant (e.g., medical tubing, medical stitches, medical stents, pacemakers, medical rods, medical plates, medical screws), any suitable pathology or damage thereof, or any suitable portion thereof.

In various aspects, an inferencing task can be performable on the medical image 104 or otherwise with respect to the anatomical structure depicted in the medical image 104. In various instances, the inferencing task can be any suitable predictive computation. As a non-limiting example, the inferencing task can be image classification, which can involve assigning the medical image 104 into one of two or more possible categories or classes (e.g., determining whether the anatomical structure of the medical image 104 belongs to a diseased class or instead to a healthy class). As another non-limiting example, the inferencing task can be image segmentation, which can involve assigning each pixel (or voxel) of the medical image 104 to a respective one of two or more possible categories or classes (e.g., determining which pixels (or voxels) of the medical image 104 belong to a tumor class and which pixels (or voxels) instead belong to a background class). As yet another non-limiting example, the inferencing task can be image-to-image regression, which can involve generating a new image based on the medical image 104 (e.g., converting the medical image 104 from one modality (X-ray) to another modality (MRI); generating a denoised version of the medical image 104; generating a quality-enhanced version of the medical image 104).

In various cases, it can be desired to perform the inferencing task on the medical image 104. It can also be desired to uncover which specific pixels (or voxels) of the medical image 104 contribute most heavily to such performance. As described herein, the attention system 102 can facilitate such objectives.

In various embodiments, the attention system 102 can comprise a processor 106 (e.g., computer processing unit, microprocessor) and a non-transitory computer-readable memory 108 that is operably or operatively or communicatively connected or coupled to the processor 106. The non-transitory computer-readable memory 108 can store computer-executable instructions which, upon execution by the processor 106, can cause the processor 106 or other components of the attention system 102 (e.g., access component 110, execution component 112, display component 114) to perform one or more acts. In various embodiments, the non-transitory computer-readable memory 108 can store computer-executable components (e.g., access component 110, execution component 112, display component 114), and the processor 106 can execute the computer-executable components.

In various embodiments, the attention system 102 can comprise an access component 110. In various aspects, the access component 110 can electronically receive or otherwise electronically access the medical image 104. In various instances, the access component 110 can electronically retrieve the medical image 104 from any suitable centralized or decentralized data structures (not shown) or from any suitable centralized or decentralized computing devices (not shown). As a non-limiting example, the access component 110 can electronically retrieve the medical image 104 from whatever medical imaging modality (e.g., CT scanner, X-ray scanner, MRI scanner, ultrasound scanner, PET scanner) generated or captured the medical image 104. In any case, the access component 110 can electronically obtain or access the medical image 104, such that other components of the attention system 102 can electronically interact with the medical image 104.

In various embodiments, the attention system 102 can comprise an execution component 112. In various aspects, the execution component 112 can execute a deep learning neural network on the medical image 104, which can yield both an inferencing task result and an attention map indicating on which specific pixels (or voxels) of the medical image 104 the deep learning neural network focused to generate the inferencing task result.

In various embodiments, the attention system 102 can comprise a display component 114. In various instances, the display component 114 can visually render the inferencing task result or the attention map on any suitable electronic display.

Figure 2:
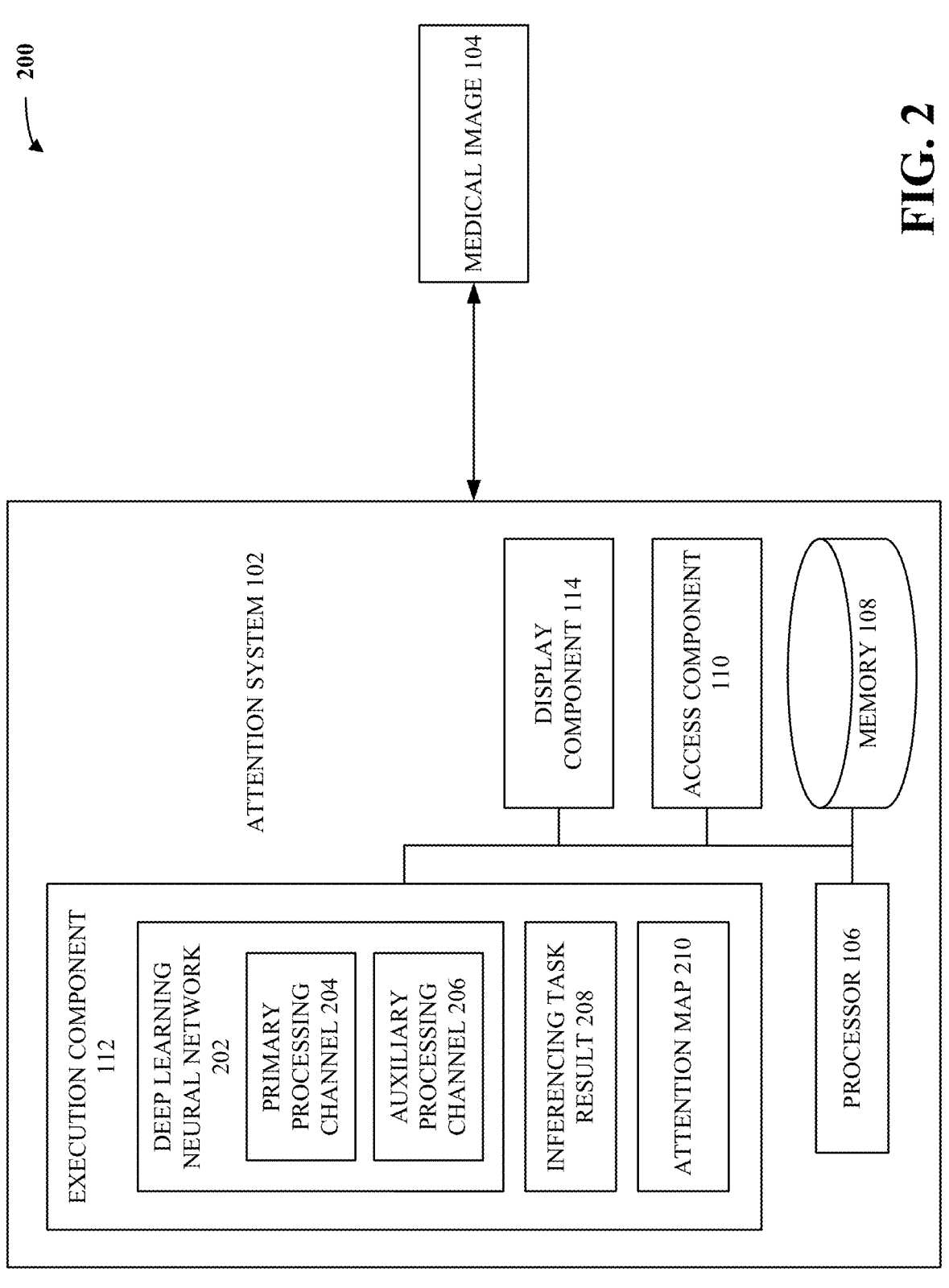
FIG. 2 illustrates a block diagram of an example, non-limiting system including a deep learning neural network, an inferencing task result, and an attention map that facilitates explainable visual attention for deep learning in accordance with one or more embodiments described herein.

FIG. 2 illustrates a block diagram of an example, non-limiting system 200 including a deep learning neural network, an inferencing task result, and an attention map that can facilitate explainable visual attention for deep learning in accordance with one or more embodiments described herein. As shown, the system 200 can, in some cases, comprise the same components as the system 100, and can further comprise a deep learning neural network 202, an inferencing task result 208, and an attention map 210.

In various embodiments, the execution component 112 can electronically store, electronically maintain, electronically control, or otherwise electronically access the deep learning neural network 202. In various aspects, the deep learning neural network 202 can comprise a primary processing channel 204 and an auxiliary processing channel 206.

In various instances, the primary processing channel 204 can have or otherwise exhibit any suitable deep learning internal architecture. For instance, the primary processing channel 204 can have an input layer, one or more hidden layers, and an output layer. In various instances, any of such layers can be coupled together by any suitable interneuron connections or interlayer connections, such as forward connections, skip connections, or recurrent connections. Furthermore, in various cases, any of such layers can be any suitable types of neural network layers having any suitable learnable or trainable internal parameters. For example, any of such input layer, one or more hidden layers, or output layer can be convolutional layers, whose learnable or trainable parameters can be convolutional kernels. As another example, any of such input layer, one or more hidden layers, or output layer can be dense layers, whose learnable or trainable parameters can be weight matrices or bias values. As still another example, any of such input layer, one or more hidden layers, or output layer can be batch normalization layers, whose learnable or trainable parameters can be shift factors or scale factors. Further still, in various cases, any of such layers can be any suitable types of neural network layers having any suitable fixed or non-trainable internal parameters. For example, any of such input layer, one or more hidden layers, or output layer can be non-linearity layers, padding layers, pooling layers, or concatenation layers.

In various cases, the auxiliary processing channel 206 can have or otherwise exhibit any suitable deep learning internal architecture. For instance, the auxiliary processing channel 206 can have an input layer, one or more hidden layers, and an output layer. In various instances, any of such layers can be coupled together by any suitable interneuron connections or interlayer connections, such as forward connections, skip connections, or recurrent connections. Furthermore, in various cases, any of such layers can be any suitable types of neural network layers having any suitable learnable or trainable internal parameters. For example, any of such input layer, one or more hidden layers, or output layer can be convolutional layers, whose learnable or trainable parameters can be convolutional kernels. As another example, any of such input layer, one or more hidden layers, or output layer can be dense layers, whose learnable or trainable parameters can be weight matrices or bias values. As still another example, any of such input layer, one or more hidden layers, or output layer can be batch normalization layers, whose learnable or trainable parameters can be shift factors or scale factors. Further still, in various cases, any of such layers can be any suitable types of neural network layers having any suitable fixed or non-trainable internal parameters. For example, any of such input layer, one or more hidden layers, or output layer can be non-linearity layers, padding layers, pooling layers, or concatenation layers.

In various aspects, the primary processing channel 204 can be considered as a trunk of the deep learning neural network 202, and the auxiliary processing channel 206 can branch off from the primary processing channel 204.

Accordingly, the auxiliary processing channel 206 can be considered as being in parallel with at least some portion (e.g., with a downstream end) of the primary processing channel 204.

In various instances, the primary processing channel 204 can be configured or trained, as described herein, to perform the inferencing task on an inputted medical image. Furthermore, the auxiliary processing channel 206 can be configured or trained, as described herein, to predict how important, significant, useful, or dispositive each specific pixel (or voxel) of such inputted medical image is with respect to performance of the inferencing task. Accordingly, in various cases, the execution component 112 can electronically execute the deep learning neural network 202 on the medical image 104, and such execution can cause the deep learning neural network 202 to produce as output both the inferencing task result 208 and the attention map 210. More specifically, such execution can cause the primary processing channel 204 to produce as output the inferencing task result 208, and such execution can cause the auxiliary processing channel 206 to produce as output the attention map 210. Various non-limiting aspects are described with respect to FIG. 3.

Figure 3:
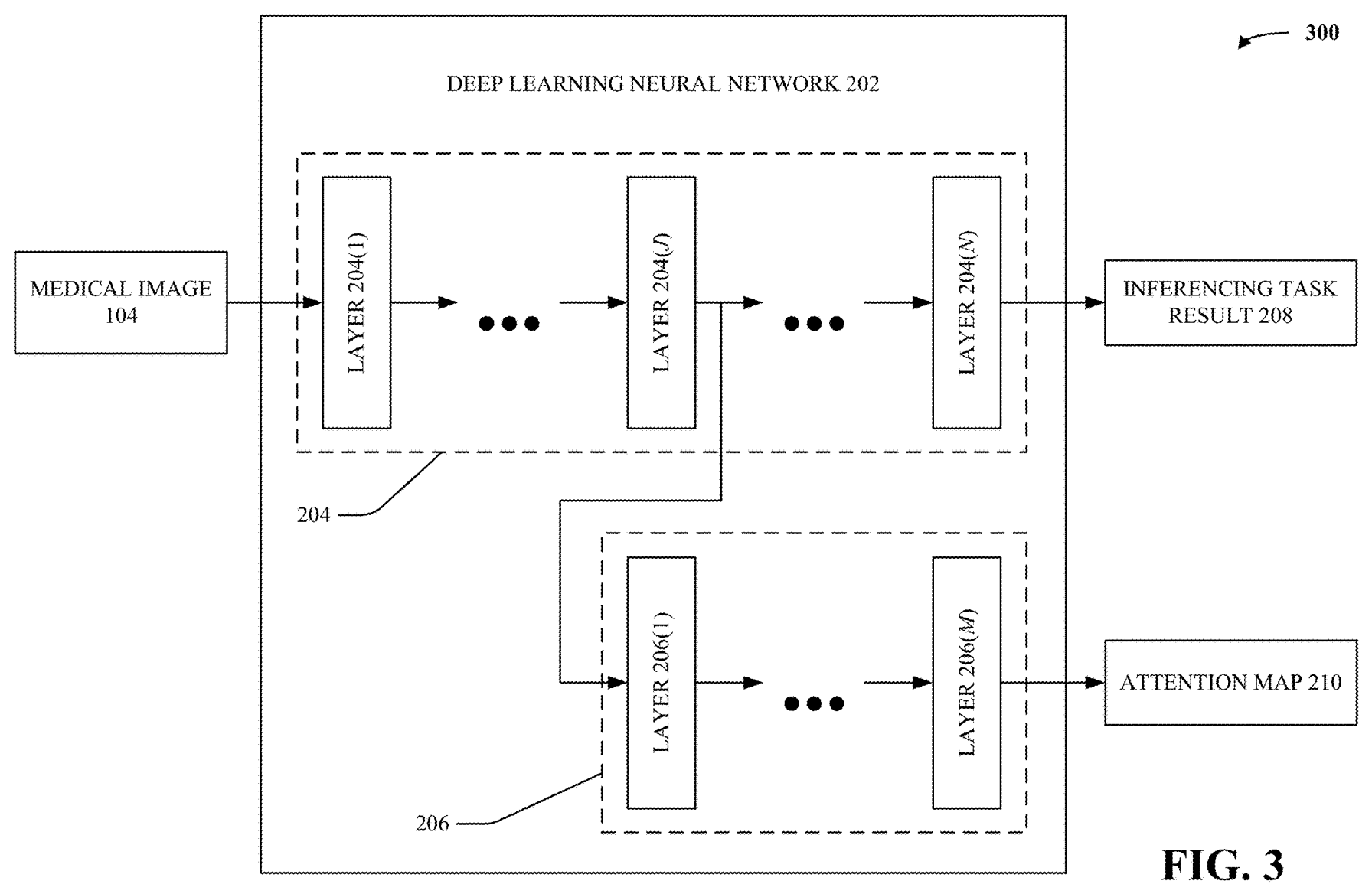

FIG. 3 illustrates an example, non-limiting block diagram 300 showing how the deep learning neural network 202 can produce the inferencing task result 208 and the attention map 210 in accordance with one or more embodiments described herein.

In various embodiments, the primary processing channel 204 can comprise n neural network layers, for any suitable positive integer n: a layer 204(1) to a layer 204(n). In various aspects, the layer 204(1) can be considered as the input layer of the primary processing channel 204, the layer 204(n) can be considered as the output layer of the primary processing channel 204, and all remaining layers (e.g., 204(2) to 204(n−1)) can be considered as hidden layers of the primary processing channel 204. As mentioned above, any of such n layers can be any suitable types of neural network layer having any suitable trainable or non-trainable internal parameters (e.g., any of such layers can be dense layers, convolutional layers, batch normalization layers, non-linearity layers, upsampling layers, downsampling layers, pooling layers, padding layers, or concatenation layers). In various instances, as shown, the layers of the primary processing channel 204 can be coupled together via forward connections, such that the activations produced by a layer 204(c) are received by a layer 204(c+1), for any suitable positive integer $1 \leq c < n$. However, this is a mere non-limiting example for ease of illustration. In various cases, any other suitable types of inter-layer connections (e.g., skip connections, recurrent connections) can be implemented in the primary processing channel 204.

In various embodiments, the auxiliary processing channel 206 can comprise m neural network layers, for any suitable positive integer m: a layer 206(1) to a layer 206(m). In various aspects, the layer 206(1) can be considered as the input layer of the auxiliary processing channel 206, the layer 206(m) can be considered as the output layer of the auxiliary processing channel 206, and all remaining layers (e.g., 206(2) to 206(m−1)) can be considered as hidden layers of the auxiliary processing channel 206. As mentioned above, any of such m layers can be any suitable types of neural network layer having any suitable trainable or non-trainable internal parameters (e.g., any of such layers can be dense layers, convolutional layers, batch normalization layers, non-linearity layers, upsampling layers, downsampling layers, pooling layers, padding layers, or concatenation layers).

In various instances, as shown, the layers of the auxiliary processing channel 206 can be coupled together via forward connections, such that the activations produced by a layer 206(d) are received by a layer 206(d+1), for any suitable positive integer 1≤d<m. However, this is a mere non-limiting example for ease of illustration. In various cases, any other suitable types of inter-layer connections (e.g., skip connections, recurrent connections) can be implemented in the auxiliary processing channel 206.

Now, in various aspects, the primary processing channel 204 can have a layer 204(j) for any suitable positive integer 1<j<n. That is, the layer 204(j) can be a hidden layer of the primary processing channel 204. In various instances, as shown, the layer 206(1) of the auxiliary processing channel 206 can be configured to receive as input whatever activations are produced by the layer 204(j). In other words, the auxiliary processing channel 206 can be considered as branching off from the primary processing channel 204 at the layer 204(j). This can cause the auxiliary processing channel 206 to be in parallel with whatever portion of the primary processing channel 204 is downstream of the layer 204(j) (e.g., to be in parallel with the layer 204(j+1) to the layer 204(n)). With this construction, the primary processing channel 204 can be considered as a foundational trunk of the deep learning neural network 202 (hence the term "primary"), and the auxiliary processing channel 206 can be considered as a secondary branch that splits off from that foundational trunk (hence the term "auxiliary").

Now, as mentioned above, the execution component 112 can electronically execute the deep learning neural network 202 on the medical image 104, and such execution can yield the inferencing task result 208 and the attention map 210. More specifically, the execution component 112 can feed the medical image 104 to the layer 204(1) of the primary processing channel 204. In various aspects, the medical image 104 can complete a forward pass through the hidden layers of the primary processing channel 204 (e.g., from the layer 204(2) to the layer 204(n−1)). In various instances, the layer 204(n) of the primary processing channel 204 can compute the inferencing task result 208, based on whatever activations the layer 204(n) receives from the layer 204(n−1) (or receives from any other layers of the primary processing channel 204 if skip connections or recurrent connections are implemented). During the forward pass through the primary processing channel 204, the layer 204(j) can, at some point, produce one or more activations. In various aspects, the one or more activations of the layer 204(j) can be fed or otherwise routed to the layer 206(1) of the auxiliary processing channel 206. In various instances, those one or more activations can complete a forward pass through the hidden layers of the auxiliary processing channel 206 (e.g., from the layer 206(2) to the layer 206(m−1)). In various cases, the layer 206(m) of the auxiliary processing channel 206 can compute the attention map 210, based on whatever activations the layer 206(m) receives from the layer 206(m−1) (or receives from any other layers of the auxiliary processing channel 206 if skip connections or recurrent connections are implemented).

In various aspects, the inferencing task result 208 can be any suitable electronic data that represents or otherwise indicates an outcome of performing the inferencing task on the medical image 104. Accordingly, the format, size, or dimensionality of the inferencing task result 208 can depend upon the inferencing task. As a non-limiting example, suppose that the inferencing task is image classification. In such case, the inferencing task result 208 can be a classification label that the primary processing channel 204 has predicted for the medical image 104. As another non-limiting example, suppose that the inferencing task is image segmentation. In such case, the inferencing task result 208 can be a pixel-wise (or voxel-wise) segmentation mask that the primary processing channel 204 has predicted for the medical image 104. As yet another non-limiting example, suppose that the inferencing task is image-to-image regression. In such case, the inferencing task result 208 can be a regressed image that the primary processing channel 204 has predicted for the medical image 104 (e.g., the inferencing task result 208 can be a predicted denoised version of the medical image 104; the inferencing task result 208 can be a predicted modality-transformed version of the medical image 104).

In various instances, the attention map 210 can be an array of attention scores, where each attention score is a scalar weight that represents or indicates how important or unimportant a respective pixel (or voxel) of the medical image 104 is with respect to the inferencing task result 208. Accordingly, the attention map 210 can exhibit the same format, size, or dimensionality as the medical image 104. As a non-limiting example, suppose that the medical image 104 is an x-by-y pixel array. In such case, the attention map 210 can be an x-by-y array of attention scores, and an attention score (i,j) of such array can be a real-valued scalar whose magnitude indicates how much or how little contribution a pixel (i,j) of the medical image 104 has in generating the inferencing task result 208, for any suitable positive integers 1≤i≤x and 1≤j≤y. As another non-limiting example, suppose that the medical image 104 is an x-by-y-by-z voxel array. In such case, the attention map 210 can be an x-by-y-by-z array of attention scores, and an attention score (i,j,k) of such array can be a real-valued scalar whose magnitude indicates how much or how little contribution a voxel (i,j,k) of the medical image 104 has in generating the inferencing task result 208, for any suitable positive integers 1≤i≤x, 1≤j≤y, and 1≤k≤z.

In various cases, the magnitude of any attention score indicated by the attention map 210 can vary continuously or discretely between any suitable minimum value (e.g., 0) indicating minimum contribution to the inferencing task and any suitable maximum value (e.g., 1) indicating maximum contribution to the inferencing task. However, this is a mere non-limiting example for ease of explanation. In various other cases, the minimum value can instead represent maximum contribution, and the maximum value can instead represent minimum contribution.

In any case, the attention map 210 can be considered as showing which particular pixels (or voxels) of the medical image 104 are more dispositive/influential or less dispositive/influential with respect to the inferencing task. In other words, the primary processing channel 204 can perform the inferencing task on the medical image 104, and the auxiliary processing channel 206 can predict which pixels (or voxels) of the medical image 104 are or were focused on the most (or the least) by the primary processing channel 204. In still other words, for any given pixel (or voxel) in the medical image 104, the auxiliary processing channel 206 can be considered guessing how much or how little the primary processing channel 204 focuses on that given pixel (or voxel). Non-limiting aspects are described with respect to FIGS. 4-5.

FIGS. 4-5 illustrate example, non-limiting instances of medical images and corresponding attention maps in accordance with one or more embodiments described herein.

First, consider FIG. 4. FIG. 4 illustrates a non-limiting example in which the medical image 104 is a two-dimensional sinogram. In this non-limiting example, the attention map 210 is a two-dimensional array having the same format, size, or dimensionality as that sinogram and showing how important or unimportant each individual pixel of that sinogram is with respect to performance of the inferencing task. In particular, darker regions of the attention map 210 can be considered as indicating, representing, or otherwise identifying pixels of the sinogram that do not strongly influence or affect the inferencing task result 208. In other words, such darker regions of the attention map 210 can be considered as showing which pixels of the sinogram are predicted or determined by the auxiliary processing channel 206 to not receive much attention or focus from the primary processing channel 204. Conversely, brighter regions of the attention map 210 can be considered as indicating, representing, or otherwise identifying pixels of the sinogram that do strongly influence or affect the inferencing task result 208. That is, such brighter regions of the attention map 210 can be considered as showing which pixels of the sinogram are predicted or determined by the auxiliary processing channel 206 to receive much attention or focus from the primary processing channel 204.

Next, consider FIG. 5. FIG. 5 illustrates a non-limiting example in which the medical image 104 is a two-dimensional CT scanned image. In this non-limiting example, the attention map 210 is a two-dimensional array having the same format, size, or dimensionality as that CT scanned image and showing how important or unimportant each individual pixel of that CT scanned image is with respect to performance of the inferencing task. In particular, darker regions of the attention map 210 can be considered as indicating, representing, or otherwise identifying pixels of the CT scanned image that do not strongly influence or affect the inferencing task result 208 (e.g., showing which pixels of the CT scanned image are predicted or determined by the auxiliary processing channel 206 to not receive much attention or focus from the primary processing channel 204). Conversely, brighter regions of the attention map 210 can be considered as indicating, representing, or otherwise identifying pixels of the CT scanned image that do strongly influence or affect the inferencing task result 208 (e.g., showing which pixels of the CT scanned image are predicted or determined by the auxiliary processing channel 206 to receive much attention or focus from the primary processing channel 204).

In any case, the execution component 112 can execute the deep learning neural network 202 on the medical image 104, and such execution can yield as output both the inferencing task result 208 and the attention map 210.

In various embodiments, the display component 114 can electronically render, on any suitable electronic display (e.g., computer screen, computer monitor), the inferencing task result 208 or the attention map 210. Accordingly, a user or technician associated with the attention system 102 can visually inspect the inferencing task result 208 or the attention map 210. Such visual inspection can allow the user or technician to become aware of not just the inferencing task result 208, but also of which particular pixels (or voxels) of the medical image 104 are determined to have contributed most heavily to the inferencing task result 208. This can be considered as providing the user or technician with clear, readily-understandable meaning or insight regarding what particular visual content illustrated by the medical image 104 had the most or least influence on the inferencing task result 208. In some cases, such meaning or insight can assist the user or technician in troubleshooting the deep learning neural network 202.

As a non-limiting example, suppose that the user or technician concludes that the inferencing task result 208 is at least partially inaccurate or incorrect. In such case, the user or technician can inspect the attention map 210. It can be possible that the attention map 210 indicates that a significant amount of attention was paid to an unexpected subset of pixels (or voxels) of the medical image 104. Accordingly, the user or technician can conclude that whatever visual content is illustrated by such unexpected subset of pixels (or voxels) distracted or otherwise threw-off the primary processing channel 204. In other words, the attention map 210 can help the user or technician to identify visual content to which the primary processing channel 204 is not agnostic but to which the primary processing channel 204 is supposed to be agnostic. In still other words, the attention map 210 can help the user or technician in identifying why the primary processing channel 204 failed to correctly analyze the medical image 104, and such identification can be used to help retrain or fine-tune the primary processing channel 204 so as to avoid similar failures in the future.

In various aspects, the display component 114 can electronically transmit the inferencing task result 208 or the attention map 210 to any other suitable computing device (not shown).

Figure 6:
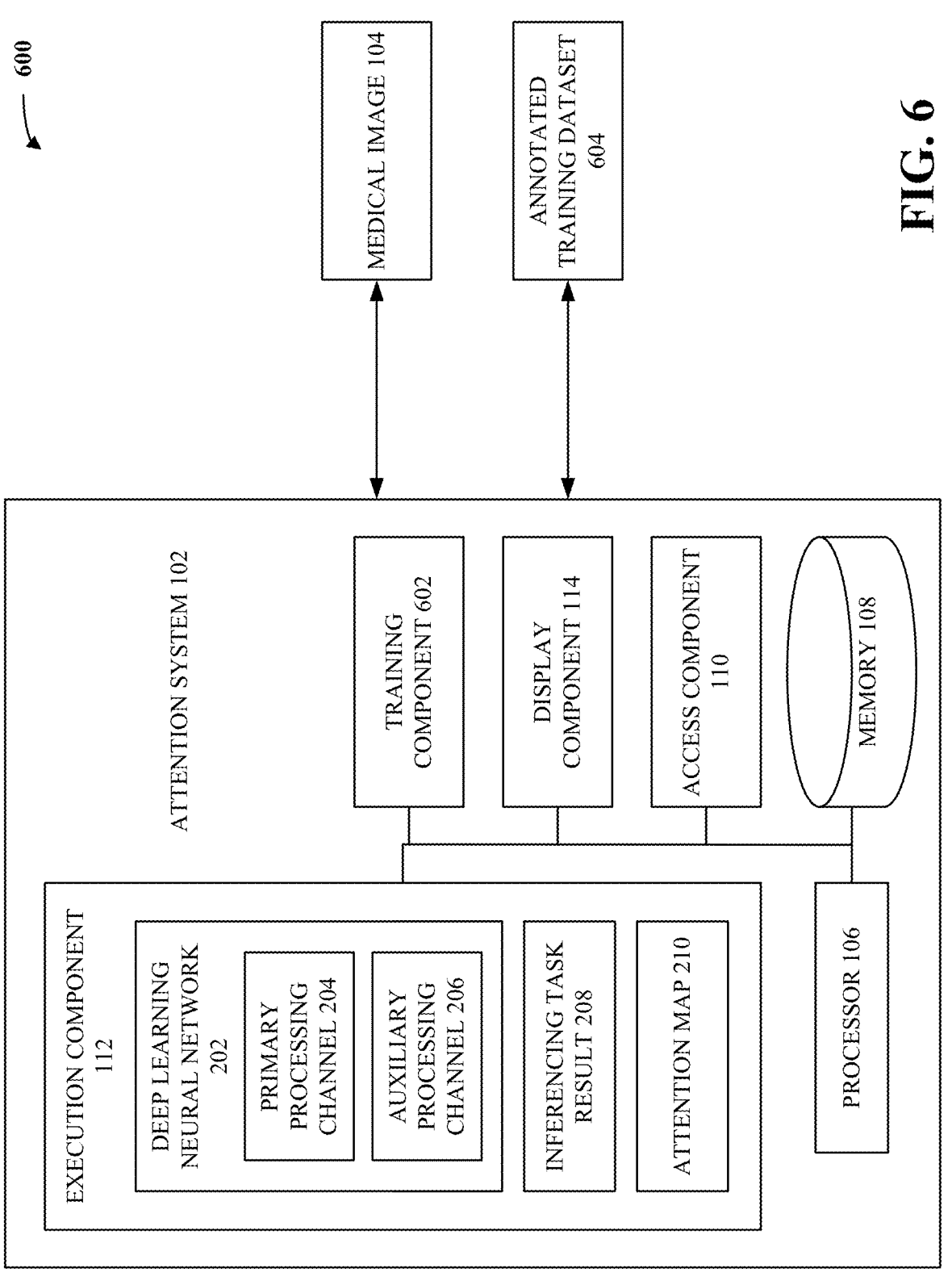
FIG. 6 illustrates a block diagram of an example, non-limiting system including a training component and an annotated training dataset that facilitates explainable visual attention for deep learning in accordance with one or more embodiments described herein.
Figure 7:
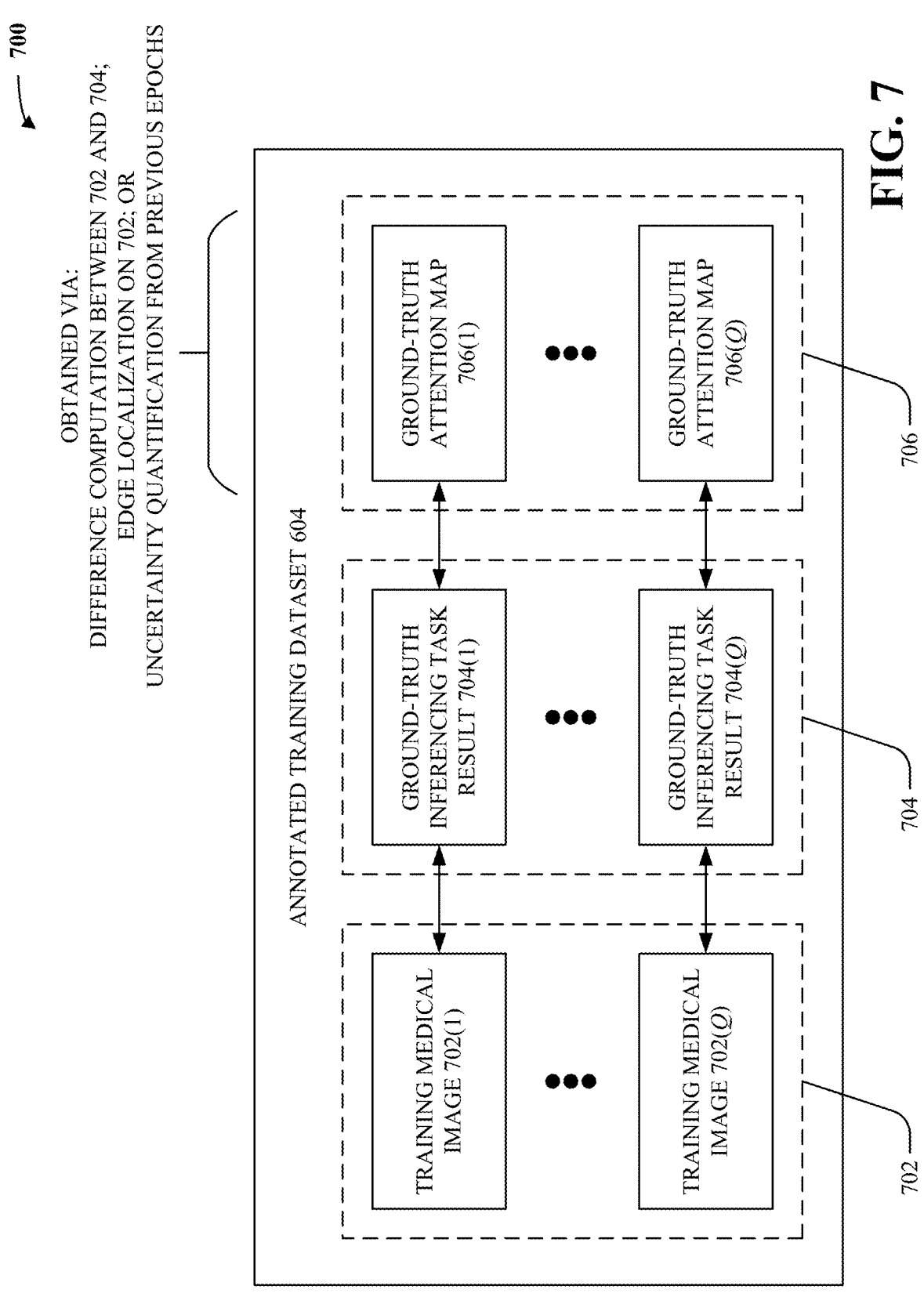
FIG. 7 illustrates an example, non-limiting block diagram of an annotated training dataset in accordance with one or more embodiments described herein.
Figure 8:
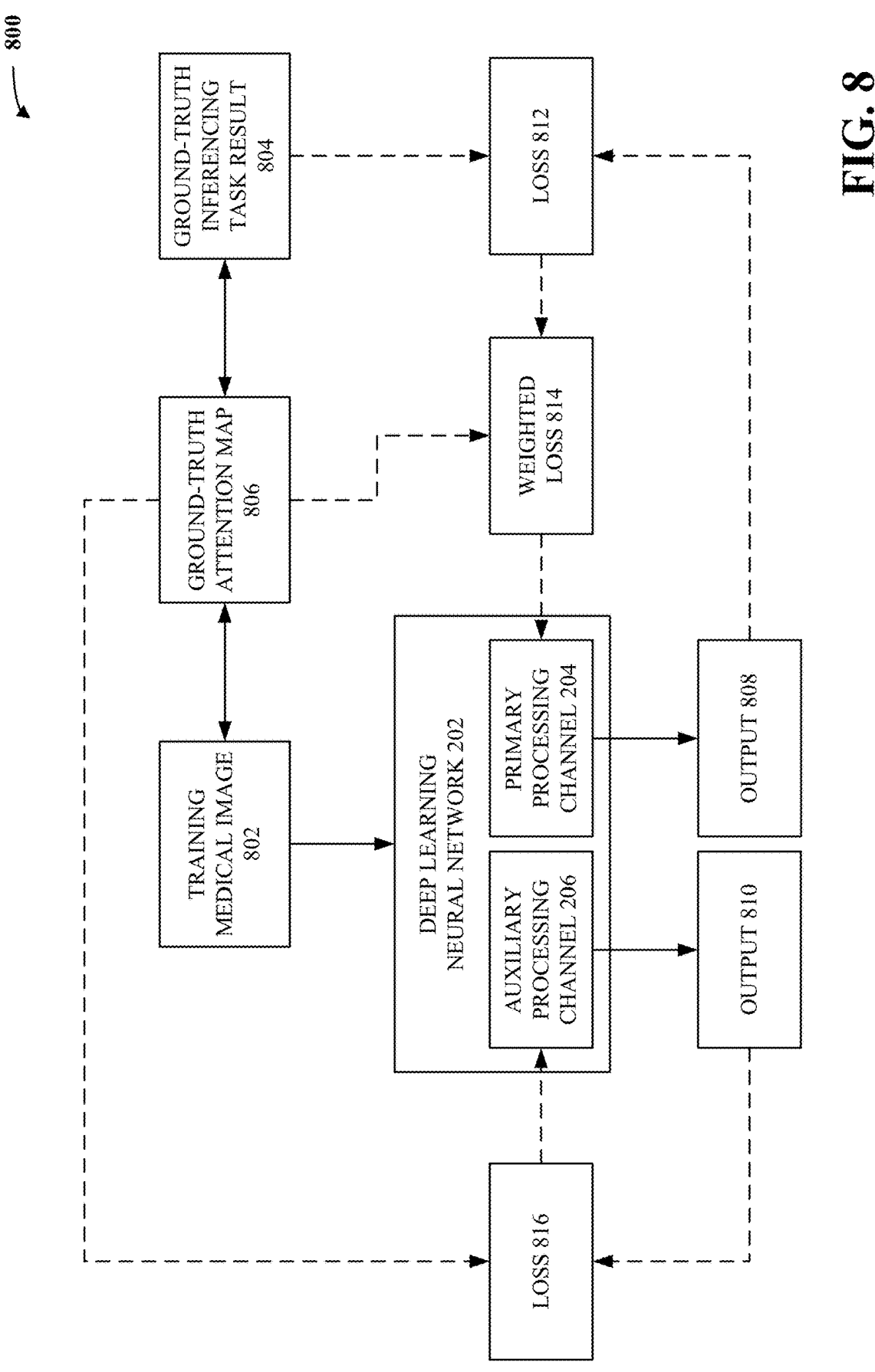
FIG. 8 illustrates an example, non-limiting block diagram showing how a deep learning neural network can be trained in accordance with one or more embodiments described herein.

In order for the inferencing task result 208 or the attention map 210 to be correct, the deep learning neural network 202 can first undergo training, as described with respect to FIGS. 6-8.

FIG. 6 illustrates a block diagram of an example, non-limiting system 600 including a training component and an annotated training dataset that can facilitate explainable visual attention for deep learning in accordance with one or more embodiments described herein. As shown, the system 600 can, in some cases, comprise the same components as the system 200, and can further comprise a training component 602 and an annotated training dataset 604.

In various embodiments, the access component 110 can electronically receive, retrieve, or otherwise access, from any suitable source, the annotated training dataset 604, and the training component 602 can electronically train the deep learning neural network 202 on the annotated training dataset 604. Various non-limiting aspects are described with respect to FIGS. 7-8.

FIG. 7 illustrates an example, non-limiting block diagram 700 of the annotated training dataset 604 in accordance with one or more embodiments described herein.

In various embodiments, the annotated training dataset 604 can comprise a set of training medical images 702. In various aspects, the set of training medical images 702 can comprise q images, for any suitable positive integer q: a training medical image 702(1) to a training medical image 702(q). In various instances, each of the set of training medical images can exhibit the same format, size, or dimensionality as the medical image 104. As a non-limiting example, suppose that the medical image 104 is an x-by-y pixel array. In such case, each of the set of training medical images 702 can likewise be an x-by-y pixel array. As another non-limiting example, suppose that the medical image 104 is an x-by-y-by-z voxel array. In such case, each of the set of training medical images 702 can likewise be an x-by-y-by-z voxel array.

In various cases, the annotated training dataset 604 can comprise a set of ground-truth inferencing task results 704. In various aspects, the set of ground-truth inferencing task results 704 can respectively correspond (e.g., in one-to-one fashion) with the set of training medical images 702.

Accordingly, since the set of training medical images 702 can comprise q images, the set of ground-truth inferencing task results 704 can comprise q inferencing task results: a ground-truth inferencing task result 704(1) to a ground-truth inferencing task result 704(q). In various cases, each of the set of ground-truth inferencing task results 704 can have the same format, size, or dimensionality as the inferencing task result 208. Indeed, in various instances, each of the set of ground-truth inferencing task results 704 can be, indicate, or otherwise represent whatever correct or accurate inferencing task result is known or deemed to correspond to a respective one of the set of training medical images 702. As a non-limiting example, the ground-truth inferencing task result 704(1) can correspond to the training medical image 702(1). Accordingly, the ground-truth inferencing task result 704(1) can be considered as the correct or accurate classification label, segmentation mask, or regression output that is known or deemed to correspond to the training medical image 702(1). As another non-limiting example, the ground-truth inferencing task result 704(q) can correspond to the training medical image 702(q). So, the ground-truth inferencing task result 704(q) can be considered as the correct or accurate classification label, segmentation mask, or regression output that is known or deemed to correspond to the training medical image 702(q).

In various aspects, the annotated training dataset 604 can comprise a set of ground-truth attention maps 706(1). In various instances, the set of ground-truth attention maps 706 can respectively correspond (e.g., in one-to-one fashion) with the set of training medical images 702. Accordingly, since the set of training medical images 702 can comprise q images, the set of ground-truth attention maps 706 can comprise q maps: a ground-truth attention map 706(1) to a ground-truth attention map 706(q). In various cases, each of the set of ground-truth attention maps 706 can have the same format, size, or dimensionality as the attention map 210. Indeed, in various instances, each of the set of ground-truth attention maps 706 can be, indicate, or otherwise represent whatever correct or accurate attention map is known or deemed to correspond to a respective one of the set of training medical images 702. As a non-limiting example, the ground-truth attention map 706(1) can correspond to the training medical image 702(1). Accordingly, the ground-truth attention map 706(1) can be considered as indicating the correct or accurate respective attention score for each individual pixel (or voxel) of the training medical image 702(1). As another non-limiting example, the ground-truth attention map 706(q) can correspond to the training medical image 702(q). Accordingly, the ground-truth attention map 706(q) can be considered as indicating the correct or accurate respective attention score for each individual pixel (or voxel) of the training medical image 702(q).

In various aspects, the set of ground-truth attention maps 706 can be obtained or otherwise generated by performing edge, boundary, or contour localization on the set of training medical images 702. After all, when given a medical image that depicts an anatomical structure, it can be the case that one or more visible edges, boundaries, or contours of that anatomical structure are particularly relevant for performing the inferencing task on that given medical image. Accordingly, there can be an edge detector (not shown). In various instances, the edge detector can be any suitable machine learning model that can be pre-trained in any suitable fashion (e.g., supervised fashion, unsupervised fashion, reinforcement learning fashion) to segment edges, boundaries, or contours that are visually perceptible in inputted images. Accordingly, the edge detector can be respectively executed on the set of training medical images 702, and the resultant segmentation masks produced by the edge detector can be respectively treated as the set of ground-truth attention maps 706. As a non-limiting example, the edge detector can be executed on the training medical image 702(1), which can cause the edge detector to produce a segmentation mask that indicates which pixels (or voxels) of the training medical image 702(1) belong to or otherwise make up visible edges, boundaries, or contours of whatever anatomical structures are depicted in the training medical image 702(1), and such segmentation mask can be treated or taken as the ground-truth attention map 706(1). As another non-limiting example, the edge detector can be executed on the training medical image 702(q), which can cause the edge detector to produce a segmentation mask that indicates which pixels (or voxels) of the training medical image 702(q) belong to or otherwise make up visible edges, boundaries, or contours of whatever anatomical structures are depicted in the training medical image 702(q), and such segmentation mask can be treated or taken as the ground-truth attention map 706(q).

Note that the above-described use of an edge detector is a mere non-limiting example of how the set of ground-truth attention maps 706 can be obtained. In other embodiments, the set of ground-truth attention maps 706 can be obtained by respectively executing any other suitable type of feature extractor on the set of training medical images 702. In such cases, the feature extractor can be trained in any suitable fashion to receive an image and to produce a segmentation mask indicating which pixels (or voxels) of that image belong to any suitable visually-perceptible feature that is depicted in that image. In other words, various embodiments described herein are not limited only to edge, boundary, or contour detection.

In various aspects, the set of ground-truth attention maps 706 can be obtained or otherwise generated by comparing the set of training medical images 702 to the set of ground-truth inferencing task results 704. Indeed, when the inferencing task is image-to-image regression, then each of the set of ground-truth inferencing task results 704 can be considered as a transformed version of a respective one of the set of training medical images 702. So, it can be the case that whatever pixels (or voxels) whose intensity values undergo the most change between the set of training medical images 702 and the set of ground-truth inferencing task results 704 are particularly relevant for performing the inferencing task. Accordingly, the set of ground-truth attention maps 706 can be obtained based on respective differences computed between the set of training medical images 702 and the set of ground-truth inferencing task results 704. As a non-limiting example, the ground-truth inferencing task result 704(1) can be subtracted from the training medical image 702(1), thereby yielding a first difference array. In various cases, the ground-truth attention map 706(1) can be equal to, or otherwise based on, a normalized, absolute-value-version of that first difference array. As another non-limiting example, the ground-truth inferencing task result 704(q) can be subtracted from the training medical image 702(q), thereby yielding a q-th difference array. In various cases, the ground-truth attention map 706(q) can be equal to, or otherwise based on, a normalized, absolute-value-version of that q-th difference array.

Note that the above-described use of matrix subtraction between the set of ground-truth inferencing task results 704 and the set of training medical images 702 is a mere non-limiting example of how the set of ground-truth attention maps 706 can be obtained. In other embodiments, the set of ground-truth attention maps 706 can be obtained by respectively computing any other suitable type of relation between the set of ground-truth inferencing task results 704 and the set of training medical images 702. In other words, various embodiments described herein are not limited only to computing subtractive differences respectively between the set of ground-truth inferencing task results 704 and the set of training medical images 702.

In various instances, the set of ground-truth attention maps 706 can be obtained or otherwise generated by measuring pixel-wise (or voxel-wise) uncertainties that the primary processing channel 204 has previously exhibited with respect to the set of training medical images 702. Indeed, when the inferencing task is image segmentation or image-to-image regression, execution of the primary processing channel 204 on a given medical image can cause the primary processing channel 204 to produce an output array (e.g., to produce a segmentation mask or a regressed image). If a ground-truth inferencing task result is available for that given medical image, then that ground-truth inferencing task result can be compared to the output array, and it can be the case that pixels (or voxels) whose intensity values differ significantly between the ground-truth inferencing task result and the output array are particularly relevant for performing the inferencing task. Accordingly, the set of ground-truth attention maps 706 can be obtained by respectively comparing the set of ground-truth inferencing task results 704 to arrays that were previously outputted by the primary processing channel 204 based on the set of training medical images 702. As a non-limiting example, it can be the case that the primary processing channel 204 was previously executed (e.g., during a previous training epoch) on the training medical image 702(1), and such execution can have yielded a first prior output array (e.g., a first prior segmentation mask or regressed image that the primary processing channel 204 predicted for the training medical image 702 (1)). In various aspects, the ground-truth inferencing task result 704(1) can be subtracted from that first prior output array, thereby yielding a first difference array. In various instances, the ground-truth attention map 706(1) can be equal to, or otherwise based on, a normalized, absolute-value-version of that first difference array. As another non-limiting example, it can be the case that the primary processing channel 204 was previously executed (e.g., during a previous training epoch) on the training medical image 702(q), and such execution can have yielded a q-th prior output array (e.g., a q-th prior segmentation mask or regressed image that the primary processing channel 204 predicted for the training medical image 702(q)). In various aspects, the ground-truth inferencing task result 704(q) can be subtracted from that q-th prior output array, thereby yielding a q-th difference array. In various instances, the ground-truth attention map 706(q) can be equal to, or otherwise based on, a normalized, absolute-value-version of that q-th difference array.

Note that the above-described techniques for obtaining the set of ground-truth attention maps 706 are mere non-limiting examples. In various other embodiments, any other suitable techniques or any other suitable information can be leveraged to generate or obtain the set of ground-truth attention maps 706 (e.g., segmentation masks generated from or otherwise associated with the set of training medical images 702 or the set of ground-truth inferencing task results 704 can be leveraged; brightness or contrast gradients exhibited within the set of training medical images 702 or the set of ground-truth inferencing task results 704 can be leveraged; metadata such as imaging energy level (kilovolt peak setting, milliamp setting) associated with the set of training medical images 702 or the set of ground-truth inferencing task results 704 can be leveraged; any other information that can reveal or influence how important or unimportant which regions of a given training medical image are can be leveraged).

Now, consider FIG. 8. FIG. 8 illustrates an example, non-limiting block diagram 800 showing how the deep learning neural network 202 can be trained in accordance with one or more embodiments described herein.

In various embodiments, the training component 602 can train the deep learning neural network 202 on the annotated training dataset 604, as follows.

Prior to such training, the training component 602 can initialize in any suitable fashion (e.g., random initialization) the trainable internal parameters (e.g., weight matrices, bias vectors, convolutional kernels) of the primary processing channel 204 and of the auxiliary processing channel 206.

In various aspects, the training component 602 can select from the annotated training dataset 604 any suitable training medical image, any suitable corresponding ground-truth inferencing task result, and any suitable corresponding ground-truth attention map. These can be respectively referred to as a training medical image 802, a ground-truth inferencing task result 804, and a ground-truth attention map 806.

In various instances, the training component 602 can electronically execute the deep learning neural network 202 on the training medical image 802, and such execution can yield both an output 808 and an output 810. More specifically, the training component 602 can feed the training medical image 802 to the layer 204(1) of the primary processing channel 204, the training medical image 802 can complete a forward pass through the hidden layers of the primary processing channel 204, and the layer 204(n) of the primary processing channel 204 can compute the output 808. Moreover, during such forward pass, the layer 204(j) of the primary processing channel 204 can compute one or more activations, such one or more activations can be fed to the layer 206(1) of the auxiliary processing channel 206, such one or more activations can complete a forward pass through the hidden layers of the auxiliary processing channel 206, and the layer 206(m) of the auxiliary processing channel 206 can compute the output 810.

Note that the format, size, or dimensionality of the output 808 can be dictated by the number, arrangement, sizes, or other characteristics of the neurons, convolutional kernels, or other internal parameters of the layer 204(n) (or of any other layers of the primary processing channel 204). Accordingly, the output 808 can be forced to have whatever format, size, or dimensionality that is desired or that is otherwise suitable for the inferencing task, by adding, removing, or otherwise adjusting characteristics of the layer 204(n) (or of any other layers of the primary processing channel 204). Thus, the output 808 can be considered as the predicted inferencing task result (e.g., predicted classification label, predicted segmentation mask, predicted regression output) that the primary processing channel 204 believes should correspond to the training medical image 802. On the other hand, the ground-truth inferencing task result 804 can be the correct or accurate inferencing task result (e.g., correct or accurate classification label, correct or accurate segmentation mask, correct or accurate regression output) that is known or deemed to correspond to the training medical image 802. In various cases, if the primary processing channel 204 has so far undergone no or little training, then the output 808 can be highly inaccurate (e.g., can be very different from the ground-truth inferencing task result 804).

Similarly, note that the format, size, or dimensionality of the output 810 can be dictated by the number, arrangement, sizes, or other characteristics of the neurons, convolutional kernels, or other internal parameters of the layer 206($m$) (or of any other layers of the auxiliary processing channel 206). Accordingly, the output 810 can be forced to have the same format, size, or dimensionality as the training medical image 802, by adding, removing, or otherwise adjusting characteristics of the layer 206($m$) (or of any other layers of the auxiliary processing channel 206). Thus, the output 810 can be considered as the predicted attention map (e.g., predicted array of pixel-wise (or voxel-wise) attention scores) that the auxiliary processing channel 206 believes should correspond to the training medical image 802. On the other hand, the ground-truth attention map 806 can be the correct or accurate attention map (e.g., correct or accurate array of pixel-wise (or voxel-wise) attention scores) that is known or deemed to correspond to the training medical image 802. Just as above, if the auxiliary processing channel 206 has so far undergone no or little training, then the output 810 can be highly inaccurate (e.g., can be very different from the ground-truth attention map 806).

In various aspects, the training component 602 can compute, via any suitable error or objective function (e.g., MAE, MSE, cross-entropy), a loss 812 between the output 808 and the ground-truth inferencing task result 804. In various instances, the training component 602 can generate a weighted loss 814, by applying point-wise multiplication and summation to the loss 812 and the ground-truth attention map 806. This can be considered as weighting the loss 812 in accordance with the pixel-wise (or voxel-wise) attention scores indicated by the ground-truth attention map 806. In various cases, the training component 602 can update the trainable internal parameters of the primary processing channel 204, by performing backpropagation (e.g., stochastic gradient descent) driven by the weighted loss 814. Note that the weighted loss 814 can be implemented no matter the internal architecture of the primary processing channel 204. In other words, pixel-wise (or voxel-wise) weighting of loss functions according to ground-truth attention maps can be considered as architecture-agnostic or otherwise as plug-and-play.

Moreover, in various aspects, the training component 602 can compute, via any suitable error or objective function (e.g., MAE, MSE, cross-entropy), a loss 816 between the output 810 and the ground-truth attention map 806. In various instances, the training component 602 can update the trainable internal parameters of the auxiliary processing channel 206, by performing backpropagation (e.g., stochastic gradient descent) driven by the loss 816.

In various aspects, the above-described training procedure can be repeated for any suitable number of training medical images (e.g., for each training medical image in the annotated training dataset 604). Such training can ultimately cause the trainable internal parameters of the primary processing channel 204 to become iteratively optimized for accurately or correctly performing the inferencing task on inputted medical images. Such training can also ultimately cause the trainable internal parameters of the auxiliary processing channel 206 to become iteratively optimized for accurately or correctly predicting how important individual pixels (or voxels) of such inputted medical images are with respect to the inferencing task (e.g., for accurately or correctly predicting which pixels (or voxels) the primary processing channel 204 will focus on).

In various cases, the training component 602 can implement any suitable training termination criterion or any suitable training batch sizes when training the deep learning neural network 202.

The discussion associated with FIG. 8 mainly describes the primary processing channel 204 and the auxiliary processing channel 206 as being trained from scratch (e.g., from random internal parameter initializations) simultaneously with each other. However, this is a mere non-limiting example for ease of illustration and explanation. In various other embodiments, it can be the case that the deep learning neural network 202 originally comprises the primary processing channel 204 and lacks the auxiliary processing channel 206. In such case, the training component 602 can train from scratch (e.g., from a random internal parameter initialization) the primary processing channel 204, using the set of training medical images 702 and the set of ground-truth inferencing task results 704. Note that such training of the primary processing channel 204 alone can, in some instances, involve leveraging the set of ground-truth attention maps 706, as described with respect to FIG. 8 (e.g., the primary processing channel 204 can be updated via backpropagation driven by the weighted loss 814). However, such training of the primary processing channel 204 alone can, in other instances, not involve the set of ground-truth attention maps 706 (e.g., the training component 602 can refrain from computing the weighted loss 814, and the primary processing channel 204 can thus be updated via backpropagation driven by the loss 812). Now, after the primary processing channel 204 has been trained in such fashion, the training component 602 can insert the auxiliary processing channel 206 into the deep learning neural network 202. After such insertion, the training component 602 can randomly initialize the trainable internal parameters of the auxiliary processing channel 206. However, because the primary processing channel 204 in such scenario can have already undergone some training, the training component 602 can refrain from randomly initializing the trainable internal parameters of the primary processing channel 204. The training component 602 can then train both the auxiliary processing channel 206 and the primary processing channel 204 as described with respect to FIG. 8. In various aspects, this can be considered as training the auxiliary processing channel 206 from scratch while fine-tuning the primary processing channel 204.

In various aspects, note that weighting the training outputs (e.g., 808) produced by the primary processing channel 204 according to the set of ground-truth attention maps 706 can significantly improve performance of the primary processing channel 204. Indeed, the inventors of various embodiments described herein experimentally verified such performance boost, as described with respect to FIGS. 9-11.

Figure 9:
Figure 10:
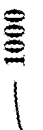

FIGS. 9-11 illustrate example, non-limiting experimental results regarding explainable visual attention for deep learning in accordance with one or more embodiments described herein.

In particular, various embodiments described herein were reduced to practice during various experiments. In such experiments, the inferencing task was image-to-image regression. More specifically, the inferencing task was conversion or transformation of low-energy CT scanned images into high-energy CT scanned images. In such experiments, a first version of the primary processing channel 204 was reduced to practice, where such first version was trained without leveraging the set of ground-truth attention maps 706. Also in such experiments, a second version of the primary processing channel 204 was reduced to practice, where such second version was trained by leveraging the set of ground-truth attention maps 706. Such experiments involved executing both the first and second versions of the primary processing channel 204 on low-energy CT scanned images for which high-energy ground-truths were available. During such experiments, the second version of the primary processing channel 204 outperformed the first version of the primary processing channel 204. In particular, the second version of the primary processing channel 204 was able to predict high-energy CT scanned images more accurately (e.g., with higher Dice scores) than the first version of the primary processing channel 204. Indeed, FIG. 9 illustrates a ground-truth high-energy image 900 corresponding to a particular low-energy CT scanned image. During such experiments, the first version of the primary processing channel 204 was executed on that particular low-energy CT scanned image, thereby yielding a predicted high-energy image 1000 as shown in FIG. 10. Also during such experiments, the second version of the primary processing channel 204 was executed on that particular low-energy CT scanned image, thereby yielding a predicted high-energy image 1100 as shown in FIG. 11. As can be seen, the predicted high-energy image 1100 is much more similar to the ground-truth high-energy image 900 than is the predicted high-energy image 1000. In other words, weighting the training loss function of the primary processing channel 204 according to the set of ground-truth attention maps 706 significantly improved the performance of the primary processing channel 204.

FIG. 12 illustrates a flow diagram of an example, non-limiting computer-implemented method 1200 that can facilitate explainable visual attention for deep learning in accordance with one or more embodiments described herein. In various cases, the attention system 102 can facilitate the computer-implemented method 1200.

In various embodiments, act 1202 can include accessing, by a device (e.g., via 110) operatively coupled to a processor (e.g., 106), a medical image (e.g., 104) generated by a medical imaging scanner.

In various aspects, act 1204 can include performing, by the device (e.g., via 112) and via execution of a deep learning neural network (e.g., 202), an inferencing task on the medical image, wherein the deep learning neural network can receive as input the medical image and can produce as output both an inferencing task result (e.g., 208) and an attention map (e.g., 210) indicating on which pixels or voxels of the medical image the deep learning neural network focused in generating the inferencing task result.

In various instances, act 1206 can include visually rendering, by the device (e.g., via 114), the inferencing task result and the attention map on an electronic display.

Although not explicitly shown in FIG. 12, the computer-implemented method 1200 can include training, by the device (e.g., via 602), the deep learning neural network on an annotated training dataset (e.g., 604). In various aspects, the deep learning neural network can comprise a first processing channel (e.g., 204) and a second processing channel (e.g., 206). In various instances, the annotated training dataset can comprise a training medical image (e.g., 802), a ground-truth inferencing task result (e.g., 804) corresponding to the training medical image, and a ground-truth attention map (e.g., 806) corresponding to the training medical image. In various cases, the training can comprise: randomly initializing, by the device (e.g., via 602), trainable internal parameters of the first processing channel and of the second processing channel; executing, by the device (e.g., via 602), the deep learning neural network on the training medical image, thereby causing the first processing channel to produce a first output (e.g., 808) and causing the second processing channel to produce a second output (e.g., 810); computing, by the device (e.g., via 602), a first loss (e.g., 812) between the ground-truth inferencing task result and the first output; weighting, by the device (e.g., via 602), the first loss via point-wise multiplication with the ground-truth attention map (e.g., thereby yielding 814); updating, by the device (e.g., via 602), the trainable internal parameters of the first processing channel, via backpropagation driven by the weighted first loss (e.g., driven by 814); computing, by the device (e.g., via 602), a second loss (e.g., 816) between the ground-truth attention map and the second output; and updating, by the device (e.g., via 602), the trainable internal parameters of the second processing channel, via backpropagation driven by the second loss.

Although not explicitly shown in FIG. 12, the inferencing task can be image-to-image regression, and the ground-truth attention map can be based on a relation between the training medical image and the ground-truth inferencing task result (e.g., as described with respect to FIG. 7).

Although not explicitly shown in FIG. 12, the inferencing task can be image segmentation or image-to-image regression, and the ground-truth attention map can be generated via execution of a feature extractor on the training medical image (e.g., as described with respect to FIG. 7).

Although not explicitly shown in FIG. 12, the inferencing task can be image segmentation or image-to-image regression, and the ground-truth attention map can indicate pixel-wise or voxel-wise uncertainties or errors exhibited by the deep learning neural network with respect to the training medical image during a previous training epoch (e.g., as described with respect to FIG. 7).

Although not explicitly shown in FIG. 12, the inferencing task result can be produced by a first processing channel (e.g., 204) of the deep learning neural network, the attention map can be produced by a second processing channel (e.g., 206) of the deep learning neural network, the second processing channel can branch off from and be in parallel to at least a portion of the first processing channel (e.g., parallel with 204($j$+1) to 204($n$)), the device (e.g., via 602) can train the first processing channel from scratch prior to the second processing channel being inserted into the deep learning neural network, and the device (e.g., via 602) can train the second processing channel from scratch while fine-tuning the first processing channel.

Although the herein disclosure mainly describes various embodiments as applying to medical images, this is a mere non-limiting example for ease of illustration and explanation. In various cases, various embodiments described herein can be applied to facilitate visual attention for any suitable images (e.g., even for non-medical images).

Various embodiments described herein can include a computer program product for facilitating explainable visual attention for deep learning. In various aspects, the computer program product can comprise a non-transitory computer-readable memory (e.g., 108) having program instructions embodied therewith. In various instances, the program instructions can be executable by a processor (e.g., 106) to cause the processor to access a deep learning neural network (e.g., 202) comprising a primary processing channel (e.g., 204), wherein the primary processing channel can be trained, using a set of training images (e.g., 702) and a set of ground-truth inferencing task results (e.g., 704) respectively corresponding to the set of training images, to perform an inferencing task. In various cases, the program instructions can be further executable to cause the processor to insert an auxiliary processing channel (e.g., 206) into the deep learning neural network, such that the auxiliary processing channel branches off from, and is in parallel to at least a portion of, the primary processing channel. In various aspects, the program instructions can be further executable to cause the processor to train, using a set of ground-truth attention maps (e.g., 706) respectively corresponding to the set of training images, the auxiliary processing channel to produce pixel-wise or voxel-wise attention maps indicating where within inputted images the deep learning neural network focuses when performing the inferencing task. In various aspects, the set of ground-truth attention maps can be based on relations between the set of training images and the set of ground-truth inferencing task results. In various other aspects, the set of ground-truth attention maps can be generated via execution of a feature extractor on the set of training images. In yet other aspects, the set of ground-truth attention maps can respectively indicate which regions of the set of training images the primary processing channel unconfidently or incorrectly analyzed in one or more previous training epochs.

As described herein, and as shown at least by FIG. 4, a sinogram can be considered as a type of image.

In various instances, machine learning algorithms or models can be implemented in any suitable way to facilitate any suitable aspects described herein. To facilitate some of the above-described machine learning aspects of various embodiments, consider the following discussion of artificial intelligence (AI). Various embodiments described herein can employ artificial intelligence to facilitate automating one or more features or functionalities. The components can employ various AI-based schemes for carrying out various embodiments/examples disclosed herein. In order to provide for or aid in the numerous determinations (e.g., determine, ascertain, infer, calculate, predict, prognose, estimate, derive, forecast, detect, compute) described herein, components described herein can examine the entirety or a subset of the data to which it is granted access and can provide for reasoning about or determine states of the system or environment from a set of observations as captured via events or data. Determinations can be employed to identify a specific context or action, or can generate a probability distribution over states, for example. The determinations can be probabilistic; that is, the computation of a probability distribution over states of interest based on a consideration of data and events. Determinations can also refer to techniques employed for composing higher-level events from a set of events or data.

Such determinations can result in the construction of new events or actions from a set of observed events or stored event data, whether or not the events are correlated in close temporal proximity, and whether the events and data come from one or several event and data sources. Components disclosed herein can employ various classification (explicitly trained (e.g., via training data) as well as implicitly trained (e.g., via observing behavior, preferences, historical information, receiving extrinsic information, and so on)) schemes or systems (e.g., support vector machines, neural networks, expert systems, Bayesian belief networks, fuzzy logic, data fusion engines, and so on) in connection with performing automatic or determined action in connection with the claimed subject matter. Thus, classification schemes or systems can be used to automatically learn and perform a number of functions, actions, or determinations.

A classifier can map an input attribute vector, $z=(z_1, z_2, z_3, z_4, Zn)$, to a confidence that the input belongs to a class, as by $f(z)=confidence$ (class). Such classification can employ a probabilistic or statistical-based analysis (e.g., factoring into the analysis utilities and costs) to determinate an action to be automatically performed. A support vector machine (SVM) can be an example of a classifier that can be employed. The SVM operates by finding a hyper-surface in the space of possible inputs, where the hyper-surface attempts to split the triggering criteria from the non-triggering events. Intuitively, this makes the classification correct for testing data that is near, but not identical to training data. Other directed and undirected model classification approaches include, e.g., naïve Bayes, Bayesian networks, decision trees, neural networks, fuzzy logic models, or probabilistic classification models providing different patterns of independence, any of which can be employed. Classification as used herein also is inclusive of statistical regression that is utilized to develop models of priority.

Figure 13:
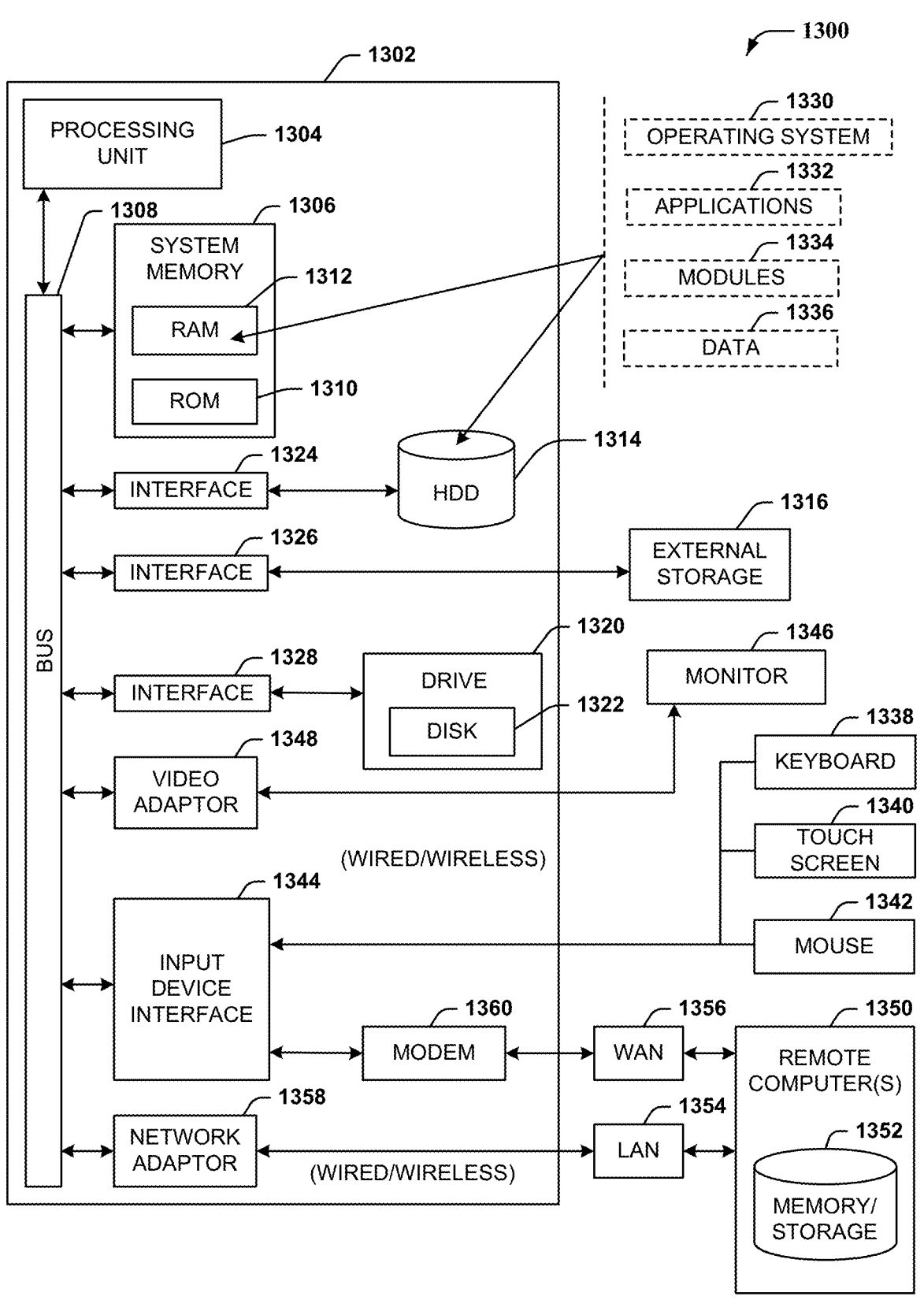
FIG. 13 illustrates a block diagram of an example, non-limiting operating environment in which one or more embodiments described herein can be facilitated.

In order to provide additional context for various embodiments described herein, FIG. 13 and the following discussion are intended to provide a brief, general description of a suitable computing environment 1300 in which the various embodiments of the embodiment described herein can be implemented. While the embodiments have been described above in the general context of computer-executable instructions that can run on one or more computers, those skilled in the art will recognize that the embodiments can be also implemented in combination with other program modules or as a combination of hardware and software.

Generally, program modules include routines, programs, components, data structures, etc., that perform particular tasks or implement particular abstract data types. Moreover, those skilled in the art will appreciate that the inventive methods can be practiced with other computer system configurations, including single-processor or multi-processor computer systems, minicomputers, mainframe computers, Internet of Things (IoT) devices, distributed computing systems, as well as personal computers, hand-held computing devices, microprocessor-based or programmable consumer electronics, and the like, each of which can be operatively coupled to one or more associated devices.

The illustrated embodiments of the embodiments herein can be also practiced in distributed computing environments where certain tasks are performed by remote processing devices that are linked through a communications network. In a distributed computing environment, program modules can be located in both local and remote memory storage devices.

Computing devices typically include a variety of media, which can include computer-readable storage media, machine-readable storage media, or communications media, which two terms are used herein differently from one another as follows. Computer-readable storage media or machine-readable storage media can be any available storage media that can be accessed by the computer and includes both volatile and nonvolatile media, removable and non-removable media. By way of example, and not limitation, computer-readable storage media or machine-readable storage media can be implemented in connection with any method or technology for storage of information such as computer-readable or machine-readable instructions, program modules, structured data or unstructured data.

Computer-readable storage media can include, but are not limited to, random access memory (RAM), read only memory (ROM), electrically erasable programmable read only memory (EEPROM), flash memory or other memory technology, compact disk read only memory (CD-ROM), digital versatile disk (DVD), Blu-ray disc (BD) or other optical disk storage, magnetic cassettes, magnetic tape, magnetic disk storage or other magnetic storage devices, solid state drives or other solid state storage devices, or other tangible or non-transitory media which can be used to store desired information. In this regard, the terms "tangible" or "non-transitory" herein as applied to storage, memory or computer-readable media, are to be understood to exclude only propagating transitory signals per se as modifiers and do not relinquish rights to all standard storage, memory or computer-readable media that are not only propagating transitory signals per se.

Computer-readable storage media can be accessed by one or more local or remote computing devices, e.g., via access requests, queries or other data retrieval protocols, for a variety of operations with respect to the information stored by the medium.

Communications media typically embody computer-readable instructions, data structures, program modules or other structured or unstructured data in a data signal such as a modulated data signal, e.g., a carrier wave or other transport mechanism, and includes any information delivery or transport media. The term "modulated data signal" or signals refers to a signal that has one or more of its characteristics set or changed in such a manner as to encode information in one or more signals. By way of example, and not limitation, communication media include wired media, such as a wired network or direct-wired connection, and wireless media such as acoustic, RF, infrared and other wireless media.

With reference again to FIG. 13, the example environment 1300 for implementing various embodiments of the aspects described herein includes a computer 1302, the computer 1302 including a processing unit 1304, a system memory 1306 and a system bus 1308. The system bus 1308 couples system components including, but not limited to, the system memory 1306 to the processing unit 1304. The processing unit 1304 can be any of various commercially available processors. Dual microprocessors and other multi-processor architectures can also be employed as the processing unit 1304.

The system bus 1308 can be any of several types of bus structure that can further interconnect to a memory bus (with or without a memory controller), a peripheral bus, and a local bus using any of a variety of commercially available bus architectures. The system memory 1306 includes ROM 1310 and RAM 1312. A basic input/output system (BIOS) can be stored in a non-volatile memory such as ROM, erasable programmable read only memory (EPROM), EEPROM, which BIOS contains the basic routines that help to transfer information between elements within the computer 1302, such as during startup. The RAM 1312 can also include a high-speed RAM such as static RAM for caching data.

The computer 1302 further includes an internal hard disk drive (HDD) 1314 (e.g., EIDE, SATA), one or more external storage devices 1316 (e.g., a magnetic floppy disk drive (FDD) 1316, a memory stick or flash drive reader, a memory card reader, etc.) and a drive 1320, e.g., such as a solid state drive, an optical disk drive, which can read or write from a disk 1322, such as a CD-ROM disc, a DVD, a BD, etc. Alternatively, where a solid state drive is involved, disk 1322 would not be included, unless separate. While the internal HDD 1314 is illustrated as located within the computer 1302, the internal HDD 1314 can also be configured for external use in a suitable chassis (not shown). Additionally, while not shown in environment 1300, a solid state drive (SSD) could be used in addition to, or in place of, an HDD 1314. The HDD 1314, external storage device(s) 1316 and drive 1320 can be connected to the system bus 1308 by an HDD interface 1324, an external storage interface 1326 and a drive interface 1328, respectively. The interface 1324 for external drive implementations can include at least one or both of Universal Serial Bus (USB) and Institute of Electrical and Electronics Engineers (IEEE) 1394 interface technologies. Other external drive connection technologies are within contemplation of the embodiments described herein.

The drives and their associated computer-readable storage media provide nonvolatile storage of data, data structures, computer-executable instructions, and so forth. For the computer 1302, the drives and storage media accommodate the storage of any data in a suitable digital format. Although the description of computer-readable storage media above refers to respective types of storage devices, it should be appreciated by those skilled in the art that other types of storage media which are readable by a computer, whether presently existing or developed in the future, could also be used in the example operating environment, and further, that any such storage media can contain computer-executable instructions for performing the methods described herein.

A number of program modules can be stored in the drives and RAM 1312, including an operating system 1330, one or more application programs 1332, other program modules 1334 and program data 1336. All or portions of the operating system, applications, modules, or data can also be cached in the RAM 1312. The systems and methods described herein can be implemented utilizing various commercially available operating systems or combinations of operating systems.

Computer 1302 can optionally comprise emulation technologies. For example, a hypervisor (not shown) or other intermediary can emulate a hardware environment for operating system 1330, and the emulated hardware can optionally be different from the hardware illustrated in FIG. 13. In such an embodiment, operating system 1330 can comprise one virtual machine (VM) of multiple VMs hosted at computer 1302. Furthermore, operating system 1330 can provide runtime environments, such as the Java runtime environment or the .NET framework, for applications 1332. Runtime environments are consistent execution environments that allow applications 1332 to run on any operating system that includes the runtime environment. Similarly, operating system 1330 can support containers, and applications 1332 can be in the form of containers, which are lightweight, standalone, executable packages of software that include, e.g., code, runtime, system tools, system libraries and settings for an application.

Further, computer 1302 can be enable with a security module, such as a trusted processing module (TPM). For instance with a TPM, boot components hash next in time boot components, and wait for a match of results to secured values, before loading a next boot component. This process can take place at any layer in the code execution stack of computer 1302, e.g., applied at the application execution level or at the operating system (OS) kernel level, thereby enabling security at any level of code execution.

A user can enter commands and information into the computer 1302 through one or more wired/wireless input devices, e.g., a keyboard 1338, a touch screen 1340, and a pointing device, such as a mouse 1342. Other input devices (not shown) can include a microphone, an infrared (IR) remote control, a radio frequency (RF) remote control, or other remote control, a joystick, a virtual reality controller or virtual reality headset, a game pad, a stylus pen, an image input device, e.g., camera(s), a gesture sensor input device, a vision movement sensor input device, an emotion or facial detection device, a biometric input device, e.g., fingerprint or iris scanner, or the like. These and other input devices are often connected to the processing unit 1304 through an input device interface 1344 that can be coupled to the system bus 1308, but can be connected by other interfaces, such as a parallel port, an IEEE 1394 serial port, a game port, a USB port, an IR interface, a BLUETOOTH® interface, etc.

A monitor 1346 or other type of display device can be also connected to the system bus 1308 via an interface, such as a video adapter 1348. In addition to the monitor 1346, a computer typically includes other peripheral output devices (not shown), such as speakers, printers, etc.

The computer 1302 can operate in a networked environment using logical connections via wired or wireless communications to one or more remote computers, such as a remote computer(s) 1350. The remote computer(s) 1350 can be a workstation, a server computer, a router, a personal computer, portable computer, microprocessor-based entertainment appliance, a peer device or other common network node, and typically includes many or all of the elements described relative to the computer 1302, although, for purposes of brevity, only a memory/storage device 1352 is illustrated. The logical connections depicted include wired/wireless connectivity to a local area network (LAN) 1354 or larger networks, e.g., a wide area network (WAN) 1356. Such LAN and WAN networking environments are commonplace in offices and companies, and facilitate enterprise-wide computer networks, such as intranets, all of which can connect to a global communications network, e.g., the Internet.

When used in a LAN networking environment, the computer 1302 can be connected to the local network 1354 through a wired or wireless communication network interface or adapter 1358. The adapter 1358 can facilitate wired or wireless communication to the LAN 1354, which can also include a wireless access point (AP) disposed thereon for communicating with the adapter 1358 in a wireless mode.

When used in a WAN networking environment, the computer 1302 can include a modem 1360 or can be connected to a communications server on the WAN 1356 via other means for establishing communications over the WAN 1356, such as by way of the Internet. The modem 1360, which can be internal or external and a wired or wireless device, can be connected to the system bus 1308 via the input device interface 1344. In a networked environment, program modules depicted relative to the computer 1302 or portions thereof, can be stored in the remote memory/storage device 1352. It will be appreciated that the network connections shown are example and other means of establishing a communications link between the computers can be used.

When used in either a LAN or WAN networking environment, the computer 1302 can access cloud storage systems or other network-based storage systems in addition to, or in place of, external storage devices 1316 as described above, such as but not limited to a network virtual machine providing one or more aspects of storage or processing of information. Generally, a connection between the computer 1302 and a cloud storage system can be established over a LAN 1354 or WAN 1356 e.g., by the adapter 1358 or modem 1360, respectively. Upon connecting the computer 1302 to an associated cloud storage system, the external storage interface 1326 can, with the aid of the adapter 1358 or modem 1360, manage storage provided by the cloud storage system as it would other types of external storage. For instance, the external storage interface 1326 can be configured to provide access to cloud storage sources as if those sources were physically connected to the computer 1302.

The computer 1302 can be operable to communicate with any wireless devices or entities operatively disposed in wireless communication, e.g., a printer, scanner, desktop or portable computer, portable data assistant, communications satellite, any piece of equipment or location associated with a wirelessly detectable tag (e.g., a kiosk, news stand, store shelf, etc.), and telephone. This can include Wireless Fidelity (Wi-Fi) and BLUETOOTH® wireless technologies. Thus, the communication can be a predefined structure as with a conventional network or simply an ad hoc communication between at least two devices.

FIG. 14 is a schematic block diagram of a sample computing environment 1400 with which the disclosed subject matter can interact. The sample computing environment 1400 includes one or more client(s) 1410. The client(s) 1410 can be hardware or software (e.g., threads, processes, computing devices). The sample computing environment 1400 also includes one or more server(s) 1430. The server(s) 1430 can also be hardware or software (e.g., threads, processes, computing devices). The servers 1430 can house threads to perform transformations by employing one or more embodiments as described herein, for example. One possible communication between a client 1410 and a server 1430 can be in the form of a data packet adapted to be transmitted between two or more computer processes. The sample computing environment 1400 includes a communication framework 1450 that can be employed to facilitate communications between the client(s) 1410 and the server(s) 1430. The client(s) 1410 are operably connected to one or more client data store(s) 1420 that can be employed to store information local to the client(s) 1410. Similarly, the server(s) 1430 are operably connected to one or more server data store(s) 1440 that can be employed to store information local to the servers 1430.

Various embodiments may be a system, a method, an apparatus or a computer program product at any possible technical detail level of integration. The computer program product can include a computer readable storage medium (or media) having computer readable program instructions thereon for causing a processor to carry out aspects of various embodiments. The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium can also include the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network or a wireless network. The network can comprise copper transmission cables, optical transmission fibers, wireless transmission, routers, firewalls, switches, gateway computers or edge servers. A network adapter card or network interface in each computing/processing device receives computer readable program instructions from the network and forwards the computer readable program instructions for storage in a computer readable storage medium within the respective computing/processing device. Computer readable program instructions for carrying out operations of various embodiments can be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions can execute entirely on the user's computer, partly on the user's computer, as a stand-alone software package, partly on the user's computer and partly on a remote computer or entirely on the remote computer or server. In the latter scenario, the remote computer can be connected to the user's computer through any type of network, including a local area network (LAN) or a wide area network (WAN), or the connection can be made to an external computer (for example, through the Internet using an Internet Service Provider). In some embodiments, electronic circuitry including, for example, programmable logic circuitry, field-programmable gate arrays (FPGA), or programmable logic arrays (PLA) can execute the computer readable program instructions by utilizing state information of the computer readable program instructions to personalize the electronic circuitry, in order to perform various aspects.

Various aspects are described herein with reference to flowchart illustrations or block diagrams of methods, apparatus (systems), and computer program products according to various embodiments. It will be understood that each block of the flowchart illustrations or block diagrams, and combinations of blocks in the flowchart illustrations or block diagrams, can be implemented by computer readable program instructions. These computer readable program instructions can be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart or block diagram block or blocks. These computer readable program instructions can also be stored in a computer readable storage medium that can direct a computer, a programmable data processing apparatus, or other devices to function in a particular manner, such that the computer readable storage medium having instructions stored therein comprises an article of manufacture including instructions which implement aspects of the function/act specified in the flowchart or block diagram block or blocks. The computer readable program instructions can also be loaded onto a computer, other programmable data processing apparatus, or other device to cause a series of operational acts to be performed on the computer, other programmable apparatus or other device to produce a computer implemented process, such that the instructions which execute on the computer, other programmable apparatus, or other device implement the functions/acts specified in the flowchart or block diagram block or blocks.

The flowcharts and block diagrams in the Figures illustrate the architecture, functionality, and operation of possible implementations of systems, methods, and computer program products according to various embodiments. In this regard, each block in the flowchart or block diagrams can represent a module, segment, or portion of instructions, which comprises one or more executable instructions for implementing the specified logical function(s). In some alternative implementations, the functions noted in the blocks can occur out of the order noted in the Figures. For example, two blocks shown in succession can, in fact, be executed substantially concurrently, or the blocks can sometimes be executed in the reverse order, depending upon the functionality involved. It will also be noted that each block of the block diagrams or flowchart illustration, and combinations of blocks in the block diagrams or flowchart illustration, can be implemented by special purpose hardware-based systems that perform the specified functions or acts or carry out combinations of special purpose hardware and computer instructions.

While the subject matter has been described above in the general context of computer-executable instructions of a computer program product that runs on a computer or computers, those skilled in the art will recognize that this disclosure also can or can be implemented in combination with other program modules. Generally, program modules include routines, programs, components, data structures, etc. that perform particular tasks or implement particular abstract data types. Moreover, those skilled in the art will appreciate that various aspects can be practiced with other computer system configurations, including single-processor or multi-processor computer systems, mini-computing devices, mainframe computers, as well as computers, hand-held computing devices (e.g., PDA, phone), microprocessor-based or programmable consumer or industrial electronics, and the like. The illustrated aspects can also be practiced in distributed computing environments in which tasks are performed by remote processing devices that are linked through a communications network. However, some, if not all aspects of this disclosure can be practiced on stand-alone computers. In a distributed computing environment, program modules can be located in both local and remote memory storage devices.

As used in this application, the terms "component," "system," "platform," "interface," and the like, can refer to or can include a computer-related entity or an entity related to an operational machine with one or more specific functionalities. The entities disclosed herein can be either hardware, a combination of hardware and software, software, or software in execution. For example, a component can be, but is not limited to being, a process running on a processor, a processor, an object, an executable, a thread of execution, a program, or a computer. By way of illustration, both an application running on a server and the server can be a component. One or more components can reside within a process or thread of execution and a component can be localized on one computer or distributed between two or more computers. In another example, respective components can execute from various computer readable media having various data structures stored thereon. The components can communicate via local or remote processes such as in accordance with a signal having one or more data packets (e.g., data from one component interacting with another component in a local system, distributed system, or across a network such as the Internet with other systems via the signal). As another example, a component can be an apparatus with specific functionality provided by mechanical parts operated by electric or electronic circuitry, which is operated by a software or firmware application executed by a processor. In such a case, the processor can be internal or external to the apparatus and can execute at least a part of the software or firmware application. As yet another example, a component can be an apparatus that provides specific functionality through electronic components without mechanical parts, wherein the electronic components can include a processor or other means to execute software or firmware that confers at least in part the functionality of the electronic components. In an aspect, a component can emulate an electronic component via a virtual machine, e.g., within a cloud computing system.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. As used herein, the term "and/or" is intended to have the same meaning as "or." Moreover, articles "a" and "an" as used in the subject specification and annexed drawings should generally be construed to mean "one or more" unless specified otherwise or clear from context to be directed to a singular form. As used herein, the terms "example" or "exemplary" are utilized to mean serving as an example, instance, or illustration. For the avoidance of doubt, the subject matter disclosed herein is not limited by such examples. In addition, any aspect or design described herein as an "example" or "exemplary" is not necessarily to be construed as preferred or advantageous over other aspects or designs, nor is it meant to preclude equivalent exemplary structures and techniques known to those of ordinary skill in the art.

The herein disclosure describes non-limiting examples. For ease of description or explanation, various portions of the herein disclosure utilize the term "each," "every," or "all" when discussing various examples. Such usages of the term "each," "every," or "all" are non-limiting. In other words, when the herein disclosure provides a description that is applied to "each," "every," or "all" of some particular object or component, it should be understood that this is a non-limiting example, and it should be further understood that, in various other examples, it can be the case that such description applies to fewer than "each," "every," or "all" of that particular object or component.

As it is employed in the subject specification, the term "processor" can refer to substantially any computing processing unit or device comprising, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures such as, but not limited to, molecular and quantum-dot based transistors, switches and gates, in order to optimize space usage or enhance performance of user equipment. A processor can also be implemented as a combination of computing processing units. In this disclosure, terms such as "store," "storage," "data store," "data storage," "database," and substantially any other information storage component relevant to operation and functionality of a component are utilized to refer to "memory components," entities embodied in a "memory," or components comprising a memory. It is to be appreciated that memory or memory components described herein can be either volatile memory or nonvolatile memory, or can include both volatile and nonvolatile memory. By way of illustration, and not limitation, nonvolatile memory can include read only memory (ROM), programmable ROM (PROM), electrically programmable ROM (EPROM), electrically erasable ROM (EEPROM), flash memory, or nonvolatile random access memory (RAM) (e.g., ferroelectric RAM (FeRAM). Volatile memory can include RAM, which can act as external cache memory, for example. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM (RDRAM). Additionally, the disclosed memory components of systems or computer-implemented methods herein are intended to include, without being limited to including, these and any other suitable types of memory.

What has been described above include mere examples of systems and computer-implemented methods. It is, of course, not possible to describe every conceivable combination of components or computer-implemented methods for purposes of describing this disclosure, but many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim.

The descriptions of the various embodiments have been presented for purposes of illustration, but are not intended to be exhaustive or limited to the embodiments disclosed. Many modifications and variations will be apparent without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A system, comprising:
   a processor that executes computer-executable instructions stored in a non-transitory computer-readable memory, wherein execution of the computer-executable instructions causes the processor to:
   access a deep learning neural network that comprises a first processing channel and a second processing channel;

access an annotated training dataset that comprises a training medical image, a ground-truth inferencing task result corresponding to the training medical image, and a ground-truth attention map indicating which pixels or voxels of the training medical image should be focused on to produce the ground-truth inferencing task result;

randomly initialize first trainable internal parameters of the first processing channel and second trainable internal parameters of the second processing channel;

execute the deep learning neural network on the training medical image, thereby causing the first processing channel to produce a first output and causing the second processing channel to produce a second output;

compute a first loss between the ground-truth inferencing task result and the first output;

weight the first loss via point-wise multiplication with the ground-truth attention map;

update the first trainable internal parameters of the first processing channel, via backpropagation driven by the weighted first loss;

compute a second loss between the ground-truth attention map and the second output; and update the second trainable internal parameters of the second processing channel, via backpropagation driven by the second loss.

2. The system of claim 1, wherein execution of the computer-executable instructions further causes the processor to:

access a medical image generated by a medical imaging scanner;

execute, after training, the deep learning neural network on the medical image, wherein the deep learning neural network receives the medical image, wherein the first processing channel produces an inferencing task result, and wherein the second processing channel produces an attention map indicating on which pixels or voxels of the medical image the deep learning neural network focused in generating the inferencing task result; and visually render the inferencing task result and the attention map on an electronic display.

3. The system of claim 1 wherein the ground-truth attention map is generated based on computing a difference array between the training medical image and the ground-truth inferencing task result.

4. The system of claim 1, wherein the ground-truth attention map is generated via execution of an edge detector on the training medical image.

5. The system of claim 1, wherein the ground-truth attention map is generated based on computing a difference array between the ground-truth inferencing task result and an output array produced by the first processing channel during a previous training epoch.

6. A computer-implemented method, comprising:

accessing, by a device operatively coupled to a processor, a deep learning neural network that comprises a first processing channel and a second processing channel;

accessing, by the device, an annotated training dataset that comprises a training medical image, a ground-truth inferencing task result corresponding to the training medical image, and a ground-truth attention map indicating which pixels or voxels of the training medical image should be focused on to produce the ground-truth inferencing task result;

randomly initializing, by the device, first trainable internal parameters of the first processing channel and second trainable internal parameters of the second processing channel;

executing, by the device, the deep learning neural network on the training medical image, thereby causing the first processing channel to produce a first output and causing the second processing channel to produce a second output;

computing, by the device, a first loss between the ground-truth inferencing task result and the first output;

weighting, by the device, the first loss via point-wise multiplication with the ground-truth attention map;

updating, by the device, the first trainable internal parameters of the first processing channel, via backpropagation driven by the weighted first loss;

computing, by the device, a second loss between the ground-truth attention map and the second output; and updating, by the device, the second trainable internal parameters of the second processing channel, via backpropagation driven by the second loss.

7. The computer-implemented method of claim 6, further comprising:

accessing, by the device, a medical image generated by a medical imaging scanner;

executing, by the device and after training, the deep learning neural network on the medical image, wherein the deep learning neural network receives the medical image, wherein the first processing channel produces an inferencing task result, and wherein the second processing channel produces an attention map indicating on which pixels or voxels of the medical image the deep learning neural network focused in generating the inferencing task result; and visually rendering, by the device, the inferencing task result and the attention map on an electronic display.

8. The computer-implemented method of claim 6, wherein the ground-truth attention map is generated based on computing a difference array between the training medical image and the ground-truth inferencing task result.

9. The computer-implemented method of claim 6, wherein the ground-truth attention map is generated via execution of an edge detector on the training medical image.

10. The computer-implemented method of claim 6, wherein the ground-truth attention map is generated based on computing a difference array between the ground-truth inferencing task result and an output array produced by the first processing channel during a previous training epoch.

11. A computer program product for facilitating explainable visual attention for deep learning, the computer program product comprising a non-transitory computer-readable memory having program instructions embodied therewith, the program instructions executable by a processor to cause the processor to:

access a deep learning neural network that comprises a first processing channel and a second processing channel;

access an annotated training dataset that comprises a training medical image, a ground-truth inferencing task result corresponding to the training medical image, and a ground-truth attention map indicating which pixels or voxels of the training medical image should be focused on to produce the ground-truth inferencing task result;

randomly initialize first trainable internal parameters of the first processing channel and second trainable internal parameters of the second processing channel;

execute the deep learning neural network on the training medical image, thereby causing the first processing channel to produce a first output and causing the second processing channel to produce a second output;

compute a first loss between the ground-truth inferencing task result and the first output;

weight the first loss via point-wise multiplication with the ground-truth attention map;

update the first trainable internal parameters of the first processing channel, via backpropagation driven by the weighted first loss;

compute a second loss between the ground-truth attention map and the second output; and update the second trainable internal parameters of the second processing channel, via backpropagation driven by the second loss.

12. The computer program product of claim 11, wherein the ground-truth attention map is generated based on computing a difference array between the training medical image and the ground-truth inferencing task result.

13. The computer program product of claim 11, wherein the ground-truth attention map is generated via execution of an edge detector on the training medical image.

14. The computer program product of claim 11, wherein the ground-truth attention map is generated based on computing a difference array between the ground-truth inferencing task result and an output array produced by the first processing channel during a previous training epoch.

*    *    *    *    *